US007863011B2

(12) United States Patent
Sirbasku

(10) Patent No.: US 7,863,011 B2
(45) Date of Patent: Jan. 4, 2011

(54) SCREENING METHOD FOR PREDICTING SUSCEPTIBILITY TO BREAST CANCER

(75) Inventor: David A. Sirbasku, Austin, TX (US)

(73) Assignee: Signe Biopharma, Inc., Irving, TX (US)

( * ) Notice: Subject to any disclaimer, the term of this patent is extended or adjusted under 35 U.S.C. 154(b) by 2318 days.

(21) Appl. No.: 10/293,440

(22) Filed: Nov. 13, 2002

(65) Prior Publication Data

US 2003/0059433 A1    Mar. 27, 2003

Related U.S. Application Data

(63) Continuation-in-part of application No. 09/852,958, filed on May 10, 2001, now abandoned, and a continuation-in-part of application No. 09/852,547, filed on May 10, 2001.

(60) Provisional application No. 60/332,920, filed on Nov. 14, 2001.

(51) Int. Cl.
*G01N 33/48* (2006.01)
*G01N 33/53* (2006.01)
*G01N 33/574* (2006.01)
*G01N 1/00* (2006.01)
*C12Q 1/00* (2006.01)

(52) U.S. Cl. .......................... 435/7.23; 435/4; 435/7.21; 436/63; 436/64; 436/174

(58) Field of Classification Search .................. 436/63, 436/64, 174; 435/4, 7.21, 7.23
See application file for complete search history.

(56) References Cited

U.S. PATENT DOCUMENTS

| 5,405,772 A | 4/1995 | Ponting |
| 6,200,547 B1 | 3/2001 | Volkonsky et al. |
| 2003/0017445 A1* | 1/2003 | Berg et al. ..................... 435/4 |

FOREIGN PATENT DOCUMENTS

| WO | WO92/13563 | 8/1992 |
| WO | WO98/04681 | 2/1998 |
| WO | WO98/08934 | 3/1998 |

OTHER PUBLICATIONS

Krajci et al. (Human Genetics 90: 215-219, 1992).*
Kaiserlian et al. (The Journal of Immunology 135(2): 1126-1131, Aug. 1985).*
Meric-Bernstam, Funda. Serum Proteomics for BRCA1-associated Breast Cancer. Annals of Surgical Oncology 11(10): 883-884, 2004.*
Stern et al. Secretory component in breast cancer. Cancer Immunology Immunotherapy 19: 226-230, 1985.*
PCT International Search Report, PCT/US01/15183 dated Nov. 20, 2002, 3 pages.
Zhihong Chen et al., *A serum-free medium for hybridoma cell culture*, Cytotechnology (1993), vol. 11, pp. 169-174, XP001117870, ISSN: 0920-9069 p. 170, media and additives; pp. 173-174.
Database Biosis 'Online! Biosciences Information Service, Philadelphia, PA US; 1992, Eby J.E. et al., *Preparation of Iron-Deficient Tissue Culture Medium by Deferoxamine-Sepharose Treatment and Application to the Differential Actions of Apotransferrin and Differic Transferrin*, Database assession No. PREV199294057133, XP002218819 cited in the application abstract & Analytical Biochemistry, vol. 203, No. 2, 1992, pp. 317-325, ISSN:0003-2697.
Database Biosis 'Online! Biosciences Information Service, Philadelphia, PA US 1993, Eby John E. et al., *Apotransferrin stimulation of thyroid hormone dependent rat pituitary tumor cell growth in serum-free chemically defined medium: Role of iron(III) chelation*, Database accession No. PREV199396113609, XP002218820 cited in application abstract & Journal of Cellular Physiology, vol. 156, No. 3, 1993, pp. 588-600, ISSN:0021-9541.
Neumannova Vera et al., *Growth of human tumor cell lines in transferrin-free, low-iron medium*, In Vitro Cellular & Developmental Biology Animal, vol. 31, No. 8, 1995, pp. 625-632, XP001118629, ISSN:1071-2690, the whole document.
C.A. Janeway et al., *Chapter 3: Structure of the Antibody Molecule and the Immunoglobulin Genes: Structural variation in immunoglobulin constant regions; Chapter 9: The Humoral Immune Response: The distribution and functions of immunoglobulin isotypes*, Immuno. Biology—The Immune System In Health and Disease, Fourth Edition, Elsevier Science Ltd./Garland Publishing (1999) pp. 104, 326-327.
R.G. Hamilton, *Chapter 3: Human Immunoglobulins*, Handbook of Human Immunology, CRC Press LLC (1997) pp. 65-109.
A.J. Alberg et al., *Epidemiology, prevention, and early detection of breast cancer [Breast]*, Current Opinion in Oncology (Nov. 1997) vol. 9, 6, pp. 505-511, PMID: 9370070 [PubMed—indexed for MEDLINE); Abstract http://www.ncbi.nlm.nih.gov/entrez/query.fcgi?cmd=Retrieve&db=PubMed&list_uids=9370070&d... printed on Feb. 15, 2003 (1 page).
A.J. Alberg et al., *Epidemiology, prevention, and early detection of breast cancer [Breast]*, Current Opinion in Oncology (Nov. 1999) vol. 11, No. 6, pp. 435, 13 pages.
J.C. Allegra et al., *Growth of a Human Breast Cancer Cell Line in Serum-Free Hormone-Supplemented Medium*, Cancer Research (Nov. 1978) vol. 38, pp. 3823-3829.
J.F. Amara et al., *17β—Estradiol Has a Biphasic Effect On GH Cell Growth*, Endocrinology, Dept. of Pharm., Endocrinology (Mar. 1983) vol. 112, No. 3, pp. 1141-1143.
T. Anttila et al., *Serotypes of Chlamydia Trachomatis and Risk For Development of Cervical Squamous Cell Carcinoma*, JAMA (Jan. 2001) vol. 285, No. 1, pp. 47-51, PMID: 11150108 [PubMed—indexed for MEDLINE); Abstract http://www.ncbi.nlm.nih.gov/entrez/query.fcgi?cmd=Retrieve&db=PubMed&list_uids=11150108&d... printed on Feb. 15, 2003 (2 pages).

(Continued)

*Primary Examiner*—Alana M Harris
(74) *Attorney, Agent, or Firm*—Woodard, Emhardt, Moriarty, McNett & Henry LLP

(57) ABSTRACT

A method to aid in identifying a familial or sporadic pattern of risk in at least one individual for developing cancer of a mucosal epithelial tissue, the method comprising screening said at least one individual for heterozygosity or homozygosity for a mutation in a gene coding for a Poly-Ig (Fc) receptor or a Poly-Ig-like (Fc) receptor capable of mediating inhibition of cancer cell growth by an immunoglobulin inhibitor. A method of treating an individual so identified includes enhancing the amount of immunoglobulin inhibitor contacting a mucosal epithelial tissue of said individual, and, especially in individuals homozygous for the defective receptor, may also include prophylactic surgery. Other methods include implementation of a risk reduction or prevention program in individuals identified as being at risk.

11 Claims, No Drawings

OTHER PUBLICATIONS

T. Anttila et al., *Serotypes of Chlamydia Trachomatis and Risk For Development of Cervical Squamous Cell Carcinoma*, JAMA (Jan. 2001) vol. 285, No. 1, pp. 47-51, (Original Contribution) 11 pages.

J.M. Zenilman, *Chlamydia and Cervical Cancer: A Real Association?* JAMA (Jan. 2001) 285, No. 1, pp. 81-83, (Editorial) 5 pages.

P.E. Gravitt et al., *Chlamydia trachomatis and Cervical Squamous Cell Carcinoma*, JAMA (Apr. 2001) vol. 285, No. 13, pp. 1703-1706, (Letters) 11 pages).

B.A. Arrick, *Therapeutic implications of the TGF-beta system*, J. Mammary Gland Biol. Neoplasia. (Oct. 1996) 1(4):391-7, PMID: 10887513 [PubMed—indexed for MEDLINE]; Abstract http://www.ncbi.nlm.nih.gov/entrez/query.fcgi?cmd=Retrieve&db=PubMed&list_uids=10887513&d... printed on Feb. 21, 2003 (1 page).

C.L. Arteaga et al., *Blockade of the Epidermal Growth Factor Receptor Inhibits Transforming Growth Factor α-Induced but Not Estrogen-Induced Growth of Hormone-Dependent Human Breast Cancer*, Molecular Endocrinology (Nov. 1988) vol. 2, No. 1 pp. 1064-1069.

C.L. Arteaga et al., *Blockade of the Type I Somatomedin Receptor Inhibits Growth of Human Breast Cancer Cells in Athymic Mice*, J. Clin. Invest. (Nov. 1989) vol. 84, pp. 1418-1423.

C.L. Arteaga et al., *The multifunctional role of transforming growth factor (TGF)-beta s on mammary epithelial cell biology*, Breast Cancer Res. Treat. 1996; 38(1):49-56, PMID: 8825122 [PubMed—indexed for MEDLINE]; Abstract; http://www.ncbi.nlm.nih.gov/entrez/query.fcgi?cmd=Retrieve&db=PubMed&list_uids=8825122&d... printed on Feb. 21, 2003 (1 page).

C.L. Arteaga et al., *Transforming Growth factor beta: potential autocrine growth inhibitor of estrogen receptor-negative human breast cancer cells*, Breast Cancer Res Treat. (Jul. 1998) 48(14):3898-904, PMID: 3164252 [PubMed—indexed for MEDLINE]; Abstract; http://www.ncbi.nlm.nih.gov/entrez/query.fcgi?cmd=Retrieve&db=PubMed&list_uids=3164252&d... printed on Feb. 21, 2003 (2 pages).

A.M. Soto, *The Role of Estrogens On The Proliferation of Human Breast Tumor Cells (MCF-7)*, J. Steroid Biochem. (1985) vol. 23, No. 1, pp. 87-94.

M.A. Bakos et al., *Expression and purification of biologically active domain I of the human polymeric immunoglobulin receptor*, Mol. Immunol. (Feb. 1994) 31(2):165-8, PMID: 8309479 [PubMed—indexed for MEDLINE]; Abstract; http://www.ncbi.nlm.nih.gov/entrez/query.fcgi?cmd=Retrieve&db=PubMed&list_uids=8309479&d... printed on Feb. 22, 2003, 1 page.

M.A. Bakos et al., *Characterization of a critical binding site for human polymeric Ig on secretory component*, J. Immunol. (Nov. 1991) 147(10):3419-26, PMID: 1940346 [PubMed—indexed for MEDLINE]; Abstract Http://www.ncbi.nlm.nih,gov/entrez/query.fcgi?cmd=Retrieve&db=PubMed&list_uids=1940346&d... printed on Feb. 20, 2003, 1 page.

M.A. Bakos et al., *A Conserved Binding Site on the Receptor for Polymeric Ig Is Homologous to CDRI of Ig Vk Domains*, J. Immunol. (Aug. 1993) vol. 151, No. 3, pp. 1346-1352.

D. Barnes et al., *Growth of a human mammary tumour cell line in a serum-free medium*, Nature, Macmillan Journals Ltd. (Oct. 1979) vol. 281, No. 5730, pp. 388-389.

J. Baselga et al., *Phase II study of weekly intravenous recombinant humanized anti-p185HER2 monoclonal antibody in patients with HER2/neu-overexpressing metastatic breast cancer*, Comment in J. Clin. Oncol. (Mar. 1996) vol. 14, No. 3, pp. 697-699, PMID: 8622019 [PubMed—indexed for MEDLINE]; Abstract; http://www.ncbi.nlm.nih.gov/entrez/query.fcgi?cmd=Retrieve&db=PubMed&list_uids=8622019&dc printed on Feb. 22, 2003, 2 pages.

V. Beral et al., *Overview of the Epidemiology of Immunodeficiency—Associated Cancers*, J. Natl. Cancer Inst. Monogr. (1998) No. 23, pp. 1-6.

P. Brandtzaeg et al., *Immunoglobulin M: Local Synthesis and Selective Secretion in patients with Immunoglobulin A Deficiency*, Science (Mar. 1968) vol. 160, pp. 789-791.

Y. Berthois et al., *Phenol red in tissue culture media is a weak estrogen: Implications concerning the study of estrogen-responsive cells in culture*, Proc. Natl. Acad. Sci. USA (Apr. 1986) vol. 83, No. 8, pp. 2496-2500.

S. Bhatia et al., *Breast Cancer and Other Second Neoplasms after Childhood Hodgkin's Disease*, N. Engl. J. Med., Mar. 21, 1996, vol. 334, No. 12, pp. 745-751 (Original Articles), 15 pages.

S.S. Donaldson et al., *Second Cancers after Hodgkin's Disease in Childhood*, N. Engl. J. Med., Mar. 21, 1996, vol. 334, No. 12, pp. 792-794 (Editorials), 4 pages.

F.E. Mirer et al., *Late Effects of Treatment for Childhood Hodgkin's Disease*, N. Engl. J. Med., Aug. 1, 1996, vol. 335, No. 5, pp. 352-355 (Correspondence), 12 pages.

I. Bieche et al., *Loss and gain of distinct regions of chromosome Iq in primary breast cancer*, Clin. Cancer Res. (Jan. 1995) vol. 1, No. 1, pp. 123-127, PMID: 9815894 [PubMed—indexed for MEDLINE], Abstract, http://www.ncbi.nlm.nih.gov/entrez/query.fcgi?cmd=Retrieve&db=PubMed&list_uids=9815894&dc..., printed on Feb. 21, 2003, 1 page.

I. Bieche et al., *Deletion mapping of Chromosomal Region Ip32-pter in Primary Breast Cancer*, Genes, Chromosomes & Cancer (Mar. 1999), vol. 24, No. 3, pp. 255-263.

R.D. Bindal et al., *Bis(4-hydroxyphenyl)(2-(phenoxysulfonyl)phenyl)methane: Isolation and Structure Elucidation of a Novel Estrogen from Commercial Preparations of Phenol Red (Phenolsulfonphthalein)*, J. Med. Chem. (Oct. 1988) vol. 31, No. 10, pp. 1978-1983.

R.D. Bindal et al., *Lipophilic Impurities, Not Phenolsulfonphthalein, Account for the Estrogenic Activity in Commercial Preparation of Phenol Red*, J. Steroid Biochem (Sep. 1988) vol. 31, No. 3, pp. 287-293.

W.P. Bocchinfuso et al., *Mammary gland development and tumorigenesis in estrogen receptor knockout mice*, J. Mammary Gland Biol. Neoplasia (Oct. 1977) vol. 2, No. 4, pp. 323-334, PMID: 10935020 [PubMed—indexed for MEDLINE], Abstract, http://www.ncbi.nlm.nih.gov/enrez/query.fcgi?cmd=Retrieve&db=PubMed&list_uids=109335020&..., printed on Feb. 21, 2003, 1 page.

E. Boder, *Ataxia-telangiectasia: some historic, clinical and athologic observations*, Birth Defects Orig. Artic. Ser. 1975;11(1):255-70, PMID: 1096982 [PubMed—indexed for MEDLINE], Abstract, http://www.ncbi.nlm.nih.gov/enrez/query.fcgi?cmd=Retrieve&db=PubMed&list_uids=1096982&... printed on Feb. 21, 2003, 1 page.

P. Bordigoni et al., *Improvement of cellular immunity and IgA production in immunodeficient children after treatment with synthetic serum thymic factor (FTS)*, Lancet (Aug. 1982) vol. 2, No. 8293, pp. 293-297, PMID: 6124716 [PubMed—indexed for MEDLINE], Abstract, http://www.ncbi.nlm.nih.gov/entrez/query.fcgi?cmd=Retrieve&db=PubMed&list_uids=6124716&... printed on Feb. 12, 2003, 1 page.

P.N. Boyaka et al., *Strategies for mucosal vaccine development*, Am. J. Trop. Med. Hyg (Apr. 1999) vol. 4 Supple., pp. 35-45, PMID: 10344675 [PubMed—indexed for MEDLINE], Abstract, http://www.ncbi.nlm.nih.gov/enrez/query.fcgi?cmd=Retrieve&db=PubMed&list_uids=10344675&... printed on Feb. 21, 2003, 1 page.

P. Brandtzaeg, *Role of J Chain and Secretory Component in Receptor-Mediated Glandular and Hepatic Transport of Immunoglobulins in Man*, Scand. J. Immunol. (Aug. 1985) vol. 22, No. 2, pp. 111-146.

P. Brandtzaeg, *Part IV. Transport of IgA and the Role of the Liver: The Secretory Immune System of Lactating Human Mammary Glands Compared With Other Exocrine Organs*, Annals N.Y. Acad. Sciences (Jun. 1983) vol. 409, pp. 353-382.

P. Brandtzaeg, *Immunoglobulin M: local synthesis and selective secretion in patients with immunoglobulin A deficiency*, Science (May 1968) vol. 160, No. 829, pp. 789-791, PMID 4171541 [PubMed—indexed for MEDLINE], Abstract, http://www,ncbi.nlm.nih.gov/enrez/query.fcgi?cmd=Retrieve&db=PubMed&list_uids=4171541&... printed on Feb. 12, 2003, 1 page.

P. Brandtzaeg, *The secretory immune system of lactating human mammary glands compared with other exocrine organs*, Annals N.Y. Acad. Sciences (Jun. 1983) vol. 409, pp. 353-382, PMID 6408971 [PubMed—indexed for MEDLINE], Abstract, http://www.ncbi.nlm.nih.gov/enrez/query.fcgi?cmd=Retrieve&db=PubMed&list_uids=6408971&... printed on Feb. 20, 2003, 1 page.

P. Brandtzaeg et al., *Direct evidence for an integrated function of J chain and secretory component in epithelial transport of immunoglobulins*, Nature (Sep. 1984) vol. 311, No. 5981, pp. 71-73.

P. Brandtzaeg, *Molecular and cellular aspects of the secretory immunoglobulin system, APMIS* (Jan. 1995) vol. 103, No. 1, pp. 1-19, PMID 7695886 [PubMed—indexed for MEDLINE], Abstract, http://www.ncbi.nlm.nih.gov/enrez/query.fcgi?cmd=Retrieve&db=PubMed&list_uids=7695886&... printed on Feb. 22, 2003, 1 page.

D.A. Bronzert et al., *Transforming growth factor-beta induces platelet-derived growth factor (PDGF) messenger RNA and PDGF secretion while inhibiting growth in normal human mammary epithelial cells*, Mol. Endocrinol (Jul. 1990) vol. 4, No. 7, pp. 981-989, PMID 2178225 [PubMed—indexed for MEDLINE], Abstract, http://www.ncbi.nlm.nih.gov/enrez/query.fcgi?cmd=Retrieve&db=PubMed&list_uids=2178225&... printed on Feb. 19, 2003, 1 page.

M.G. Brattain et al., *Defects of TGF-beta receptor signaling in mammary cell tumorigenesis*, J. Mammary Gland Biol. Neoplasia (Oct. 1996) vol. 1, No. 4, pp. 365-372, PMID 10887510 [PubMed—indexed for MEDLINE], Abstract, http://www.ncbi.nlm.nih.gov/enrez/query.fcgi?cmd=Retrieve&db=PubMed&list_uids=10887510&... printed on Feb. 21, 2003, 1 page.

J.W. Brewer et al., *Mechanism and subcellular localization of secretory IgM polymer assembly*, J. Biol. Chem. (Jun. 1994) vol. 269, No. 25, pp. 17338-17348.

P. Briand et al., *Long-Term Cultivation of a Human Breast Cancer Cell Line, MCF-7, in a Chemically Defined Medium. Effect of Estradiol*, Anticancer Research (Jan.-Feb. 1986) vol. 6, No. 1, pp. 85-90.

J. Brolin et al., *Immunohistochemistry and biochemistry in detection of androgen, progesterone, and estrogen receptors in benign and malignant human prostatic tissue*, Prostate (1992) vol. 20, No. 4, pp. 281-295, PMID 1376911 [PubMed—indexed for MEDLINE], Abstract, http://www.ncbi.nlm.nih.gov/enrez/query.fcgi?cmd=Retrieve&db=PubMed&list_uids=1376911&... printed on Feb. 20, 2003, 1 page.

J.C. Cambier, *Inhibitory receptors abound?* Proc. Natl. Acad. Sci. USA (Jun. 1997) vol. 94, No. 12, pp. 5993-5995.

L.A. Castagnetta et al., *Human prostate cancer: a direct role for oestrogens*, Ciba Found Symp (1995) vol. 191, pp. 269-286; discussion pp. 286-289, PMID 8582203 [PubMed—indexed for MEDLINE], Abstract, http://www.ncbi.nlm.nih.gov/enrez/query.fcgi?cmd=Retrieve&db=PubMed&list_uids=8582203&... printed on Feb. 20, 2003, 1 page.

D. Chakravarthy et al., *Expression and secretion of TGF-beta isoforms and expression of TGF-beta-receptors I, II and III in normal and neoplastic human breast*, Int. J. Oncol. (Jul. 1999) vol. 15, No. 1, pp. 187-194, PMID 10375614 [PubMed—indexed for MEDLINE], Abstract, http://www.ncbi.nlm.nih.gov/enrez/query.fcgi?cmd=Retrieve&db=PubMed&list_uids=10375614&... printed on Feb. 22, 2003, 1 page.

D. Chalbos et al., *Estrogens stimulate cell proliferation and induce secretory proteins in a human breast cancer cell line (T47D)*, J. Clin. Endocrinol. Metab. (Aug. 1982) vol. 55, No. 2, pp. 276-283.

T.R. Chen et al., *WiDr is a derivative of another colon adenocarcinoma cell line, HT-29*, Cancer Genet Cytogenet (Jul. 1987) vol. 1, pp. 125-134, PMID 3472642 [PubMed—indexed for MEDLINE], Abstract, http://www.ncbi.nlm.nih.gov/enrez/query.fcgi?cmd=_Retrieve&db=PubMed&list_uids=3472642&... printed on Feb. 19, 2003, 1 page.

M.E. Conley et al., *Intravascular and mucosal immunoglobulin A: two separate but related systems of immune defense?* Ann Intern Med. (Jun. 1987) vol. 106, No. 6, pp. 892-899, PMID 3579073 [PubMed—indexed for MEDLINE], Abstract, http://www,ncbi.nlm.nih.gov/enrez/query.fcgi?cmd=Retrieve&db=PubMed&list_uids=3579073&... printed on Feb. 22, 2003, 1 page.

P. Corvol et al., *Species Distribution of Testosterone-Binding Globulin*, Biol. Reprod. (Apr. 1973) vol. 8, No. 3, pp. 277-282.

J.F. Couse et al., *Estrogen Receptor Null Mice: What Have We Learned and Where Will They Lead Us?* Endocrine Reviews (Jun. 1999) vol. 20, No. 3, pp. 358-417.

M. Daeron, *Fc Receptor Biology*, Annu. Rev. Immunol. (1997) vol. 15, pp. 203-234.

D.A. Damassa et al., *Biological Effects of Sex Hormone-Binding Globulin on Androgen-Induced Proliferation and Androgen Metabolism in LNCaP Prostate Cells*, Endocrinology (Jul. 1991) vol. 29, No. 1, pp. 75-84.

C.W. Daniel et al., *The role of TGF-beta in patterning and growth of the mammary ductal tree*, J. Mammary Gland Biol. Neoplasia (Oct. 1996) vol. 1, No. 4, pp. 331-341, PMID 10887507 [PubMed—indexed for MEDLINE], Abstract, http://www.ncbi.nlm.nih.gov/enrez/query.fcgi?cmd=Retrieve&db=PubMed&list_uids=10887507&... printed on Feb. 21, 2003, 1 page.

D. Danielpour et al., *Growth of MTW9/PL2 Estrogen-Responsive Rat Mammary Tumor Cells in Hormonally Defined Serum-Free Media*, In Vitro Cell Dev. Biol. (Jan. 1988) vol. 24, No. 1, pp. 42-52.

P. Darbre et al., *Effect of Estradiol On Human Breast Cancer Cells in Culture*, Cancer Research (Jan. 1983), vol. 43, No. 1, pp. 349-354.

P.D. Darbre et al., *Effects of Estradiol and Tamoxifen on Human Breast Cancer Cells in Serum-free Culture*, Cancer Research (Jul. 1984) vol. 44, No. 7, pp. 2790-2793.

G. Del Giudice et al., *Mucosal Delivery of Vaccines*, Methods (Sep. 1999) vol. 19, No. 1, pp. 148-155.

R.B. Dickson et al., *Estrogenic Regulation of Growth and Poly peptide Growth Factor Secretion in Human Breast Carcinoma*, Endocrine Reviews (Feb. 1987) vol. 8, No. 1, pp. 29-43.

R.B. Dickson et al., *Induction of epidermal growth factor-related polypeptides by 17 beta-estradiol in MCF-7 human breast cancer cells*, Endocrinology (Jan. 1986) vol. 118, No. 1, pp. 138-142, PMID 3000728 [PubMed—indexed for MEDLINE], Abstract, http://www.ncbi.nlm.nih.gov/enrez/query.fcgi?cmd=Retrieve&db=PubMed&list_uids=3000728&... printed on Feb. 19, 2003, 1 page.

R.B. Dickson et al., *Chapter 8: Estrogen Receptor-Mediated Processes in Normal and Cancer Cells*, J. Natl. Cancer Inst. Monogr. (2000) No. 27, pp. 135-145.

C.T. Eastment et al., *Human Platelet lysate Contains Growth Factor Activities for Established Cell Lines Derived From Various Tissues of Several Species*, In Vitro (1980) vol. 16, No. 8, pp. 694-705.

J.E. Eby et al., *Apotransferrin Stimulation of Thyroid Hormone Dependent Rat Pituitary Tumor Cell Growth in Serum-Free Chemically Defined Medium: Role of FE(III) Chelation*, J. Cellular Physiology (Sep. 1993) vol. 156, No. 3, pp. 588-600.

J.E. Eby et al., *Preparation of Iron-Deficient Tissue Culture Medium by Deferoxamine-Sepharose Treatment and Application to the Differential Actions of Apotransferrin and Differric Transferrin*, Anal. Biochem. (Jun. 1992) vol. 203, No. 2, pp. 317-325.

K. el-Bayoumy et al., *Comparative tumorigenicity of benzo[a]pyrene, 1-nitropyrene and 2-amino-1-methyl-6-phenylimidazo[4,5-b]pyridine administered by gavage to female CD rats*, Carcinogenesis (Feb. 1995) vol. 16, No. 2, pp. 431-434.

L.W. Engel et al., *Establishment and Characterization of Three New Continuous Cell Lines Derived from Human Breast Carcinomas*, Cancer Research (Oct. 1978), vol. 38, No. 10, pp. 3352-3364.

E. Enmark et al., *Oestrogen receptors—an overview*, J. Intern. Med. (Aug. 1999) No. 146, pp. 133-138.

E. Enmark et al., *Human Estrogen Receptor β-Gene Structure, Chromosomal Localization, and Expression Pattern*, J. Clin. Endocrinol. Metab. (Dec. 1997) vol. 82, No. 12, pp. 4258-4265.

R.H. Evans, *The Steroid and Thyroid Hormone Receptor Superfamily*, Science (May 1988) vol. 240, No. 4854, pp. 889-895, PMID 3283939 [PubMed—indexed for MEDLINE], Abstract, http://www.ncbi.nlm.nih.gov/enrez/query.fcgi?_cmd=Retrieved&db=PubMed&list_uids=3283939&... printed on Feb. 20, 2003, 1 page.

E. Fallgreen-Gebauer et al., *The covalent Linkage of Secretory Component to IgA. Structure of sIgA*, Biol. Chem. (Nov. 1993) vol. 374, No. II, pp. 1023-1028.

P. Femlund et al., *A Simple Two-Step Procedure for the Simultaneous Isolation of Corticosteroid Binding Globulin and Sex Hormone Binding Globulin from Human Serum by Chromatography on Cortisol-Sepharose and Phenyl-Sepharose*, J. Steroid Biochem (Jun. 1981) vol. 14, No. 6, pp. 545-552.

L. Fiore et al., *Poliovirus Sabin Type 1 Neutralization Epitopes Recognized by Immunoglobulin A Monoclonal Antibodies*, J. Virol. (Sep. 1997) vol. 71, No. 9, pp. 6905-6912.

B. Fisher et al., *Tamoxifen for Prevention of Breast Cancer: Report of the National Surgical Adjuvant Breast and Bowel Project P-1 Study*, J. Natl. Cancer Inst., Articles (Sep. 1998) vol. 90, No. 18, pp. 1371-1388.

W.H. Fridman, *Fc receptors and immunoglobulin binding factors*, FASEB J. (Sep. 1991) vol. 5, No. 12, pp. 2684-2690, PMID 1916092 [PubMed—indexed for MEDLINE], Abstract, http://www.ncbi.nlm.nih.gov/enrez/query.fcgi?cmd=_Retrieve&db=PubMed&list_uids=1916092&... printed on Feb. 15, 2003, 1 page.

S.A. Fuqua et al., *Variant human breast tumor estrogen receptor with constitutive transcriptional activity*, Cancer Res. (Jan. 1991) vol. 51, No. 1, pp. 105-109, PMID 1988075 [PubMed—indexed for MEDLINE], Abstract, http://www.ncbi.nlm.nih.gov/enrez/query.fcgi?cmd=_Retrieve&db=PubMed&list_uids=1988075&... printed on Feb. 20, 2003, 1 page.

S.A. Fuqua et al., *Inhibition of estrogen receptor action by a naturally occurring variant in human breast tumors*, Cancer Res. (Jan. 1992) vol. 52, No. 2, pp. 483-486, PMID 1728420 [PubMed—indexed for MEDLINE], Abstract, http://www.ncbi.nlm.nih.gov/enrez/query.fcgi?cmd=_Retrieve&db=PubMed&list_uids=1728420&... printed on Feb. 20, 2003, 1 page.

S.A. Fuqua et al., *Expression of Wild-Type Estrogen Receptor Beta and Variant Isoforms in Human Breast Cancer*, Cancer Res. (Nov. 1999) vol. 59, No. 21, pp. 5425-5428.

R.W. Furlanetto et al., *Somatomedin-C Receptors and Growth Effects in Human Breast Cells Maintained in Long-Term Tissue Culture*, Cancer Res. (May 1984) vol. 44, No. 5, pp. 2122-2128.

V. Giguere et al., *Identification of a new class of steroid hormone receptors*, Nature (Jan. 1988) vol. 331, No. 6151, pp. 91-94, PMID 3267207 [PubMed—indexed for MEDLINE], Abstract, http://www.ncbi.nlm.nih.gov/enrez/query.fcgi?cmd=_Retrieve&4=PubMed&list_uids=3267207&... printed on Feb. 12, 2003, 1 page.

H. Gobbi et al., *Transforming Growth Factor-Beta and Breast Cancer Risk in Woman With Mammary Epithelial Hyperplasia*, J. Natl. Cancer Inst. (Dec. 1999) vol. 91, No. 24, pp. 2096-2101.

D. Gospodarowicz et al., *Heparin protects basic and acidic FGF from inactivation*, J. Cell Physiol. (Sep. 1986) vol. 128, No. 3, pp. 475-484, PMID 3528177 [PubMed—indexed for MEDLINE], Abstract, http://www.ncbi.nlm.nih.gov/enrez/query.fcgi?cmd=_Retrieve&db=PubMed&list_uids=3528177&... printed on Feb. 20, 2003, 1 page.

M.L. Graham et al., *T47DCO cells, genetically unstable and containing estrogen receptor mutations, are a model for the progression of breast cancers to hormone resistance*, Cancer Res. (Oct. 1990) vol. 50, No. 19, pp. 6208-6217, PMID 2400987 [PubMed—indexed for MEDLINE], Abstract, http://www.ncbi.nlm.nih.gov/enrez/query.fcgi?cmd=_Retrieve&db=PubMed&list_uids=2400987&... printed on Feb. 20, 2003, 1 page.

J.A. Gustafsson, *Seeking Ligands for Lonely Orphan Receptors*, Science (May 1999) 284(5418):1285-6, Science (May 1999) 284(5418):1362-5, Science (May 1999) 284(5418):1365-8.

J.A. Gustafsson, *Estrogen receptor beta—a new dimension in estrogen mechanism of action*, J. Endocrinol (Dec. 1999) vol. 163, No. 3, pp. 379-383.

J.A. Gustafsson et al., *Estrogen receptor beta in the breast: role in estrogen responsiveness and development of breast cancer*, J. Steroid Biochem Mol. Biol. (Nov. 2000) vol. 74, No. 5, pp. 245-248.

J.M. Hall et al., *Linkage of Early-Onset Familial Breast Cancer to Chromosome 17q21*, Science (Dec. 1990) vol. 250, No. 4988, pp. 1684-1689.

E. Haug et al., *Receptors for 17beta-estradiol in prolactin-secreting rat pituitary cells*, Mol. Cell Endocrinol (Oct. 1978) vol. 12, No. 1, pp. 81-95, PMID 569089 [PubMed—indexed for MEDLINE], Abstract, http://www.ncbi.nlm.nih.gov/enrez/query.fcgi?cmd=_Retrieve&db=PubMed&list_uids=569089&... printed on Feb. 19, 2003, 1 page.

I.C. Henderson et al., *The relationship between prognostic and predictive factors in the management of breast cancer*, Breast Cancer Res. Treat (1998) vol. 52, No. 1-3, pp. 261-288, PMID 10066087 [PubMed—indexed for MEDLINE], Abstract, http://www.ncbi.nlm.nih.gov/enrez/query.fcgi?cmd=Retrieve&db=PubMed&list_uids=10066087&... printed on Feb. 21, 2003, 1 page.

J.S. Horoszewicz et al., *LNCaP model of human prostatic carcinoma*, Cancer Res. (Apr. 1983) vol. 43, No. 4, pp. 1809-1818.

K.B. Horwitz et al., *Steroid Receptor Analyses of Nine Human Breast Cancer Cell Lines*, Cancer Res. (Aug. 1978) vol. 38, No. 8, pp. 2434-2437.

M. Hosobuchi, *Effects of transforming growth factor beta on growth of human mammary epithelial cells in culture*, In Vitro Cell Dev Biol (Aug. 1989) vol. 24, No. 8, pp. 705-713, PMID 2548988 [PubMed—indexed for MEDLINE], Abstract, http://www.ncbi.nlm.nih.gov/enrez/query.fcgi?cmd=Retrieved&db=PubMed&list_uids=2548988&... printed on Feb. 21, 2003, 1 page.

S. Jackson et al., *Normal human sera contain antibodies directed at Fab of IgA*, J Immunol (Apr. 1987) vol. 138, No. 7, pp. 2244-2248, PMID 3494062 [PubMed—indexed for MEDLINE], Abstract, http://www.ncbi.nlm.nih.gov/enrez/query.fcgi?cmd=_Retrieve&db=PubMed&list_uids=3494062&... printed on Feb. 21, 2003, 1 page.

N. Janin et al., *Breast cancer risk in ataxia telangiectasia (AT) heterozygotes: haplotype study in French AT families*, Br J Cancer (Jun. 1999) vol. 80, No. 7, pp. 1042-1045, PMID 10362113 [PubMed—indexed for MEDLINE], Abstract, http://www.ncbi.nlm.nih.gov/enrez/query.fcgi?cmd=Retrieve&db=PubMed&list_uids=10362113&... printed on Feb. 21, 2003, 1 page.

E. Haug, *Progesterone suppression of estrogen-stimulated prolactin secretion and estrogen receptor levels in rat pituitary cells*, Endocrinology (Feb. 1979) vol. 104, No. 2, pp. 429-437, PMID 109280 [PubMed—indexed for MEDLINE], Abstract, http://www.ncbi.nlm.nih.gov/enrez/query.fcgi?cmd=Retrieve&db=PubMed&list_uids=109280&... printed on Feb. 19, 2003, 1 page.

J. Gorski et al., *Hormone receptors: studies on the interaction of estrogen with the uterus*, Recent Prog Horm Res. (1968) vol. 24, pp. 45-80, PMID 4885833 [PubMed—indexed for MEDLINE], Abstract, http://www.ncbi.nlm.nih.gov/enrez/query.fcgi?cmd=_Retrieve&db=PubMed&list_uids=4885833&... printed on Feb. 20, 2003, 1 page.

K. el-Bayoumy, *Environmental carcinogens that may be involved in human breast cancer etiology*, Chem Res. Toxicol (Sep.-Oct. 1992) vol. 5, No. 5, pp. 585-590, PMID 1445997 [PubMed—indexed for MEDLINE], Abstract, http://www.ncbi.nlm.nih.gov/enrez/query.fcgi?cmd=_Retrieve&db=PubMed&list_uids=1445997&... printed on Feb. 21, 2003, 1 page.

D.F. Easton et al., *The genetic epidemiology of BRCAI. Breast Cancer Linkage Consortium*, Lancet (Sep. 1994) vol. 344, No. 8924, pp. 761, PMID 7915813 [PubMed—indexed for MEDLINE], Abstract, http://www.ncbi.nlm.nih.gov/enrez/query.fcgi?cmd=_Retrieve&db=PubMed&list_uids=7915813&... printed on Feb. 15, 2003, 1 page.

S.C. Brooks et al., *Estrogen receptor in a human cell line (MCF-7) from breast carcinoma*, J Biol Chem (Sep. 1973) vol. 248, No. 17, pp. 6251-6253, PMID 4353636 [PubMed—indexed for MEDLINE], Abstract, http://www.ncbi.nlm.nih.gov/enrez/query.fcgi?cmd=_Retrieve&db=PubMed&list_uids=4353636&... printed on Feb. 19, 2003, 1 page.

W.S. Bullough, *Chalone control mechanisms*, Life Sci (Feb. 1975) vol. 16, No. 3, pp. 323-330, PMID 123999 [PubMed—indexed for MEDLINE], Abstract, http://www.ncbi.nlm.nih.gov/enrez/query.fcgi?cmd=Retrieve&db=PubMed&list_uids=123999&... printed on Feb. 21, 2003, 1 page.

E.V. Jensen et al., *A two-step mechanism for the interaction of estradiol with rat uterus*, Proc Natl. Acad. Sci USA (Feb. 1968) vol. 59, No. 2, pp. 632-638, PMID 5238991 [PubMed—indexed for MEDLINE], Abstract, http://www.ncbi.nlm.nih.gov/enrez/query.fcgi?cmd=_Retrieve&db=PubMed&list_uids=5238991&... printed on Feb. 20, 2003, 1 page.

E.V. Jensen et al., *Estrogen-receptor interaction*, Science (Oct. 1973) vol. 182, No. 108, pp. 126-134, PMID 4354173 [PubMed—indexed for MEDLINE], Abstract, http://www.ncbi.nlm.nih.gov/enrez/query.fcgi?cmd=Retrieve&db=PubMed&list_uids=4354173&... printed on Feb. 20, 2003, 1 page.

F.E. Johansen et al., *Role of J Chain in Secretory Immunoglobulin Formation*, Scand. J. Immunol. (Sep. 2000) vol. 52, No. 3, pp. 240-248.

M.E. Kaighn et al., *Establishment and characterization of a human prostatic carcinoma cell line (PC-3)*, Invest Urol. (Jul. 1979) No. 1, pp. 16-23, PMID 447482 [PubMed—indexed for MEDLINE], Abstract, http://www.ncbi.nlm.nih.gov/enerz/query.fcgi?cmd=_Retrieve&db=PubMed&list_uids=447482&... printed on Feb. 19, 2003, 1 page.

M. Kaufmann, *Review of known prognostic variables*, Recent Results Cancer Res. (1996) vol. 140, pp. 77-87, PMID 8787079 [PubMed—indexed for MEDLINE], Abstract, http://www.ncbi.nlm.nih.gov/enrez/query.fcgi?cmd=Retrieve&db=PubMed&list_uids=8787079&... printed on Feb. 21, 2003, 1 page.

K.P. Karey et al., *Differential Responsiveness of Human Breast Cancer Cell Lines MCF-7 and T47D to Growth Factors and 17 Beta-Estradiol*, Cancer Res. (Jul. 1988) vol. 48, No. 14, pp. 4083-4092.

J.L. Kelsey et al., *Epidemiology of Breast Cancer*, Epidemiol Rev (1990), vol. 12, pp. 228-240.

R. Kemler et al., *In vitro studies on the selective binding of IgG from different species to tissue section s of the bovine mammary glands*, Eur J. Immunol (Sep. 1975) vol. 5, No. 9, pp. 603-608, PMID 11993319 [PubMed—indexed for MEDLINE], Abstract, http://www.ncbi.nlm.nih.gov/enrez/query.fcgi?cmd=Retrieve&db=PubMed&list_uids=11993319&... printed on Feb. 15, 2003, 1 page.

N. J. Kenney et al., *Expression of Transforming Growth Factor Alpha Antisense mRNA Inhibits the Estrogen-Induced Production of TGF Alpha and Estrogen-Induced Proliferation of Estrogen-Responsive Human Breast Cancer Cells*, J. Cell Physiol (Sep. 1993) vol. 156, No. 3, pp. 497-514.

R.S. Kerbel et al., *Analysis of established human carcinoma cell lines for lynmphoreticular-associated membrane receptors*, Int. J. Cancer (Nov. 1977) vol. 20, No. 5, pp. 673-679, PMID 924690 [PubMed—indexed for MEDLINE], Abstract, http://www,ncbi.nlm.nih.gov/enrez/query.fcgi?cmd=Retrieve&db=PubMed&list_uids=924690&... printed on Feb. 21, 2003, 1 page.

I. Keydar et al., Establishment and characterization of a cell line of human breast carcinoma origin, Eur J. Cancer (May 1979), vol. 15, No. 5, pp. 659-670.

M.S. Khan et al., *Size isomers of testosterone-estradiol-binding globulin exist in the plasma of individual men and women*, Steroids (May 1985), vol. 45, No. 5, pp. 463-472, PMID 3834662 [PubMed—indexed for MEDLINE], Abstract, http://www.ncbi.nlm.nih.gov/enrez/query.fcgi?cmd=Retrieve&db=PubMed&list_uids=3834662&... printed on Feb. 21, 2003, 1 page.

K Kim et al., *Immunoglobulin G Subclasses in Human Colostrum, Milk and Saliva*, Acta Paediatr (Feb. 1992) vol. 81, No. 2, pp. 113-118, PMID 1515753 [PubMed—indexed for MEDLINE], Abstract, http://www.ncbi.nlm.nih.gov/enrez/query.fcgi?cmd= Retrieve&db=PubMed&list_uids=1515753&... printed on Feb. 15, 2003, 1 page.

W.L. Kirkland et al., *Control of Cell Growth. III. Direct Mitogenic Effect of Thyroid Hormones on an Estrogen-Dependent Rat Pituitary Tumor Cell Line*, J. Natl. Cancer Inst. (Jun. 1976) vol. 56, No. 6, pp. 1159-1164.

C. Knabbe et al., *Evidence that transforming growth factor-beta is a hormonally regulated negative growth factor in human breast cancer cells*, Cell (Feb. 1987) vol. 48, No. 3, pp. 417-428, PMID 2879636 [PubMed—indexed for MEDLINE], Abstract, http://www.ncbi.nlm.nih.gov/enrez/query.fcgi?cmd=Retrieve&db=PubMed&list_uids=2879636&... printed on Feb. 19, 2003, 1 page.

H. Kondoh et al., *Jacalin, a jackfruit lectin, precipitates IgA1 but not IgA2 subclass on gel diffusion reaction*, J. Immunol Methods (Apr. 1986) vol. 88, No. 2, pp. 171-173, PMID 3082992 [PubMed—indexed for MMEDLINE], Abstract, http://www.ncbi.nlm.nih.gov/enrez/query.fcgi?cmd=_Retrieve&db=PubMed&list_uids=3082992&... printed on Feb. 21, 2003, 1 page.

H. Kubagawa et al., *A novel pair of immunoglobulin-like receptors expressed by B cells and myeloid cells*, Proc Natl. Acad. Sci USA (May 1997) vol. 94, No. 12, pp. 5993-5995.

M. Krainer et al., *Differential contributions of BRCA1 and BRCA2 to early-onset breast cancer*, N Engl J Med (May 1997) vol. 336, No. 20, pp. 1416-1421, (Original Articles) 12 pages.

P. Krajci et al., *Molecular cloning and exon-intron mapping of the gene encoding human transmembrance secretory component (the poly-Ig receptor)*, Eur J Immunol (Sep. 1992) vol. 22, No. 9, pp. 2309-2315.

P. Krajci et al., *Secretory component mRNA and protein expression of colorectal adenomas an carcinomas*, Br J Cancer (Jun. 1996) vol. 73, No. 12, pp. 1503-1510.

P. Krajci et al., *The gene encoding human transmembrane secretory component (locus PIGR) is linked to DIS58 on chromosome I*, Hum Genet (Nov. 1992) vol. 90, No. 3, pp. 215-219, PMID 1487233 [PubMed—indexed for MEDLINE], Abstract, http://www.ncbi.nlm.nih.gov/enrez/query.fcgi?cmd=Retrieve&db=PubMed&list_uids=1487233&... printed on Feb. 21, 2003, 1 page.

P. Krajci et al., *The human transmembrane secretory component (poly-Ig receptor): molecular cloning, restriction fragment length polymorphism and chromosomal sublocalization*, Hum Genet (Oct. 1991) vol. 87, No. 6, pp. 642-648.

P. Krajci et al., *Cloning, chromosomal localization, and linkage analysis of the gene encoding human transmembrane secretory component (the poly-Ig receptor)*, Adv Exp. Med Biol (1995) No. 371A, pp. 617-623, PMID 8526003 [PubMed—indexed for MEDLINE], Abstract, http://www.ncbi.nlm.nih.gov/enrez/query.fcgi?cmd=Retrieve&db=PubMed&list_uids=8526003&... printed on Feb. 21, 2003, 1 page.

G.G. Kuiper et al., *Cloning of a novel receptor expressed in rat prostate and ovary*, Proc Natl. Acad. Sci USA (Jun. 1996) vol. 93, No. 12, pp. 5925-5930.

G.G. Kuiper et al., *Interaction of estrogen chemicals and phytoestrogens with estrogen receptor beta*, Endocrinology (Oct. 1998) vol. 139, No. 10, pp. 4252-4263.

G.G. Kuiper et al., *Comparison of the ligand binding specificity and transcript tissue distribution of estrogen receptors alpha and beta*, Endocrinology (Mar. 1997) vol. 138, No. 3, pp. 863-870.

R. Kumar et al., *The structure of nuclear hormone receptors*, Steroids (May 1999) vol. 64, No. 5, pp. 310-319.

I. Laursen et al., *Serum albumin as a modulator on growth of the human breast cancer cell line, MCF-7*, Anticancer Res. (Mar.-Apr. 1990) vol. 10, No. 2A, pp. 343-351, PMID 2346307 [PubMed—indexed for MEDLINE], Abstract, http://www.ncbi.nlm.nih.gov/enrez/query.fcgi?cmd=Retrieve&db=PubMed&list_uids=2346307&... printed on Feb. 12, 2003, 1 page.

P. Lemieux et al., *The Role of the Estrogen Receptor in Tumor Progression*, J. Steroid Biochem Mol Biol (Jan. 1996), vol. 56, Nos. 1-6, pp. 87-91.

J.J. Letterio et al., *Regulation of Immune Responses by TGF-beta*, Annu Rev Immunol, No. 16, pp. 137-161.

C. Lengauer et al., *Genetic instability in colorectal cancers*, Nature (Apr. 1997), vol. 386, No. 6625, pp. 623-627 [Letter] 10 pages.

L.M. Loomes et al., *Purification and characterization of human immunoglobulin IgA1 and IgA2 isotypes from serum*, J Immunol Methods (Aug. 1991) vol. 141, No. 2, pp. 209-218, PMID 1880427 [PubMed—indexed for MEDLINE], Abstract, http://www.ncbi.nlm.nih.gov/enrez/query.fcgi?cmd=Retrieve&db=PubMed&list_uids=1880427&... printed on Feb. 21, 2003, 1 page.

M.L. Loupart et al., *Allelic imbalance on chromosome I in human breast cancer. I. Minisatellite and RFLP analysis*, Genes Chromosomes Cancer (Jan. 1995) vol. 12, No. 1, pp. 16-23, PMID 7534106 [PubMed—indexed for MEDLINE], Abstract, http://www.ncbi.nlm.nih.gov/enrez/query.fcgi?cmd=Retrieve&db=PubMed&list_uids=7534106&... printed on Feb. 21, 2003, 1 page.

E. Lullau et al., *Antigen Binding Properties of Purified Immunoglobulin A and Reconstituted Secretory Immunoglobulin A Antibodies*, J Biol Chem (Jul. 1996) vol. 271, No. 27, pp. 16300-0.

S. Mathew et al., *Transforming growth factor receptor gene TGFBR2 maps to human chromosome band 3p22*, Genomics (Mar. 1994) vol. 20, No. 1, pp. 114-115, PMID 8020936 [PubMed—indexed for MEDLINE], Abstract, http://www.ncbi.nlp.nih.gov/enrez/query.fcgi?cmd=_Retrieve&db=PubMed&list_uids=8020936&... printed on Feb. 21, 2003, 1 page.

M.I. McBurney et al., *Colonic carcinogenesis: the microbial feast or famine mechanism*, Nutr Cancer (1987) vol. 10, No. 1-2, pp. 23-28, PMID 3039469 [PubMed—indexed for MMEDLINE], Abstract, http://www.ncbi.nlm.nih.gov/enrez/query.fcgi?cmd=Retrieve&db=PubMed&list_uids=3039469&... printed on Feb. 15, 2003, 1 page.

J. Mestecky et al., *Immunoglobulin A (IgA): Molecular and Cellular Interactions Involved in IgA Biosynthesis and Immune Response*, Adv Immunol (1987) vol. 40, pp. 153-245.

J. Mestecky et al., *Evaluation of monoclonal antibodies with specificity for human IgA, IgA subclasses and allotypes and secretory component. Results of an IUIS/WHO collaborative study*, J Immunol Methods (Jun. 1996), vol. 193, No. 2, pp. 103-148.

J.E. Moreno-Cuevas et al., *Estrogen mitogenic action. III. Is phenol red a "red herring"?*, In Vitro Cell Dev Biol Anim (Jul.-Aug. 2000) vol. 36, No. 7, pp. 447-464.

W.L. McKeehan et al., *Frontiers in Mammalian Cell Culture*, In Vitro Cell Dev Biol (Jan. 1990) vol. 26, No. 1, pp. 9-23.

S. Mosselman et al., *ER beta: identification and characterization of a novel human estrogen receptor*, FEBS Lett (Aug. 1996) vol. 392, No. 1, pp. 49-53, PMID 8769313 [PubMed—indexed for MEDLINE], Abstract, http://www.ncbi.nlm.nih.gov/enrez/query.fcgi?cmd=Retrieve&db=PubMed&list_uids=8769313&... printed on Feb. 20, 2003, 1 page.

L.C. Murphy et al., *Variant estrogen receptor mRNA species detected in human breast cancer biopsy sample*, Mol Endocrinol (Apr. 1989) vol. 3, No. 4, pp. 687-693, PMID 2725532 [PubMed—indexed for MEDLINE], Abstract, http://www.ncbi.nlm.nih.gov/enrez/query.fcgi?cmd=Retrieve&db=PubMed&list_uids=2725532&... printed on Feb. 20, 2003, 1 page.

A.M. Nakhla et al., *Induction of adenylate cyclase in a mammary carcinoma cell line by human corticosteroid-binding globulin*, Biochem Biophys Res. Commun (Jun. 1988) vol. 153, No. 3, pp. 1012-1018, PMID 2839166 [PubMed—indexed for MEDLINE], Abstract, http://www.ncbi.nlm.nih.gov/enrez/query.fcgi?cmd=Retrieve&db=PubMed&list_uids=2839166&... printed on Feb. 19, 2003, 1 page.

A.M. Nakhla et al., *Characterization of ALVA-41 cells, a new human prostatic cancer cell line*, Steroids (Oct. 1994) vol. 10, pp. 586-589.

K.A. Nathavitharana et al., *Presence of secretory IgA antibodies to an enteric bacterial pathogen in human milk and saliva*, Arch Dis Child Fetal Neonatal Ed (Mar. 1995) vol. 72, No. 2, pp. F102-F106, (Original Article) 8 pages.

J.R. Nevens et al., *Affinity Chromatographic Purification of Immunoglobulin M Antibodies Utilizing Immobilized Mannan Binding Protein*, J Chromatogr (Apr. 1992) vol. 597, Nos. 1-2, pp. 247-256.

F.R. Ochsendorf, *Infections in the male genital tract and reactive oxygen species*, Hum Reprod Update (Sep.-Oct. 1999) vol. 5, No. 5, pp. 399-420, PMID 10582780 [PubMed—indexed for MEDLINE], Abstract, http://www.ncbi.nlm.nih.gov/enrez/query.fcgi?cmd=Retrieve&db=PubMed&list_uids=10582780&... printed on Feb. 22, 2003, 1 page.

M. Ogasawara et al., *A new serum-free method of measuring growth factor activities for human breast cancer cells in culture*, In Vitro Cell Dev Biol (Sep. 1988) vol. 24, No. 9, pp. 911-920.

J.H. Olsen et al., *Cancer in Patients With Ataxia-Telangiectasia and In Their Relatives in the Nordic Countries*, J Natl. Cancer Inst. (Jan. 2001) vol. 93, No. 2, pp. 121-127.

B.W. O'Malley et al., *Female steroid hormones and target cell nuclei*, Science (Feb. 1974) vol. 183, No. 125, pp. 610-620, PMID 4359082 [PubMed—indexed for MEDLINE], Abstract, http://www.ncbi.nlm.nih.gov/enrez/query.fcgi?cmd=Retrieve&db=PubMed&list_uids=4359082&... printed on Feb. 20, 2003, 1 page.

C.K. Osborne, *Steroid hormone receptors in breast cancer management*, Breast Cancer Res. Treat (1998) vol. 51, No. 3, pp. 227-238, PMID 10068081 [PubMed—indexed for MEDLINE], Abstract, http://www.ncbi.nlm.nih.gov/enrez/query.fcgi?cmd=Retrieve&db=PubMed&list_uids=10068081&... printed on Feb. 21, 2003, 2 pages.

T.D. Pack, *Bacterial binding protein for single-step purification of human IgA*, Application Note (Apr. 1999), pp. 16, 18.

M.A. Palladino et al., *The transforming growth factor-betas. A new family of immunoregulatory molecules*, Ann NY Acad. Sci (1990) vol. 593, pp. 181-187, PMID 2197960 [PubMed—indexed for MEDLINE], Abstract, http://www.ncbi.nlm.nih.gov/enrez/query.fcgi?cmd=Retrieve&db=PubMed&list_uids=2197960&... printed on Feb. 12, 2003, 1 page.

B. Peitersen et al., *Quantitative Determination of Immunoglobulins, lysozyme, and Certain Electrolytes in breast Milk During the Entire Period of Lactation, During a 24-hour Period, and in Milk from the Individual Mammary Gland*, Acta Paediatr Scand (Sep. 1975), vol. 64, No. 5, pp. 709-717.

U. Pfeffer et al., *Estrogen receptor variant messenger RNA lacking exon 4 in estrogen-responsive human breast cancer cell lines*, Cancer Res. (Feb. 1993) vol. 53, No. 4, pp. 741-743, PMID 7916651 [PubMed—indexed for MEDLINE], Abstract, http://www.ncbi.nlm.nih.gov/enrez/query.fcgi?cmd=Retrieve&db=PubMed&list_uids=7916651&... printed on Feb. 20, 2003, 1 page.

M. Raghavan et al., *Fc Receptors and Their Interactions With Immunoglobulins*, Annu. Rev. Cell Dev. Biol. (1996) vol. 12, pp. 181-220.

R.R. Reddel et al., *Differential Sensitivity of Human Breast Cancer cell Lines to the Growth-Inhibitory Effects of Tamoxifen*, Cancer Res. (Apr. 1985) vol. 45, No. 4, pp. 1525-1531.

C.C. Reese et al., *Alternative models for estrogen and androgen regulation of human breast cancer cell (T47D) growth*, Ann NY Acad. Sci (1988) vol. 538, pp. 112-121, PMID 3190080 [PubMed—indexed for MEDLINE], Abstract, http://www.ncbi.nlm.nih.gov/enrez/query.fcgi?cmd=Retrieve&db=PubMed&list_uids=3190080&... printed on Feb. 12, 2003, 1 page.

I. Laursen et al., *Serum Albumin as a Modulator on Growth of the Human Breast Cancer Cell Line, MCF-7*, Anticancer Research (1990) vol. 10, pp. 343-352.

C.B. Reimer et al., *Specificity and association constants of 33 monoclonal antibodies to human IgA epitopes*, Immunol Lett (Jun. 1989) vol. 21, No. 3, pp. 209-215, PMID 2475439 [PubMed—indexed for MEDLINE], Abstract, http://www.ncbi.nlm.nih.gov/enrez/query.fcgi?cmd=Retrieve&db=PubMed&list_uids=2475439&... printed on Feb. 22, 2003, 1 page.

M. Reiss et al., *Transforming growth factor-beta in breast cancer: a working hypothesis*, Breast Cancer Res. Treat (Aug. 1997) vol. 45, No. 1, pp. 81-95, PMID 9285120 [PubMed—indexed for MEDLINE], Abstract, http://www.ncbi.nlm.nih.gov/enrez/query.fcgi?cmd=Retrieve&db=PubMed&list_uids=9285120&... printed on Feb. 21, 2003, 1 page.

J.M. Renoir et al., *Hormonal and immunological aspects of the phylogeny of sex steroid binding plasma protein*, Proc Natl. Acad. Sci USA (Aug. 1980) vol. 77, No. 8, pp. 4578-4582.

J.L. Reny et al., *Human Serum Does Not Contain a High Affinity Estrogen-Binding Glycoprotein Different From Sex Hormone-Binding Globulin*, J Clin Endocrinol Metab (May 1989) vol. 68, No. 5, pp. 938-945.

S.F. Retta et al., *Purification of fibronectin from human plasma*, Methods Mol Biol (1999) vol. 96, pp. 119-124, PMID 10098128 [PubMed—indexed for MEDLINE], Abstract, http://www.ncbi.nlm.nih.gov/enrez/query.fcgi?cmd=Retrieve&db=PubMed&list_uids=10098128&... printed on Mar. 12, 2003, 1 page.

A. Richardson, *Is breast cancer caused by late exposure to a common virus?* Med Hypotheses (Jun. 1997) vol. 48, No. 6, pp. 491-497, PMID 9247892 [PubMed—indexed for MEDLINE], Abstract, http://www.ncbi.nlm.nih.gov/enrez/query.fcgi?cmd=Retrieve&db=PubMed&list_uids=9247892&... printed on Feb. 22, 2003, 1 page.

T.L. Riss et al., *Rat Pituitary Tumor Cells in Serum-Free Culture. II. Serum Factor and Thyroid Hormone Requirements for Estrogen-Responsive Growth*, In Vitro Cell Dev Biol. (Feb. 1989) vol. 25, No. 2, pp. 136-142.

T.L. Riss et al., *Purification and Identification of Transferrin as a Major Pituitary-Derived Mitogen for MTW9/PL2 Rat Mammary Tumor Cells*, In Vitro Cell Dev Biol (Dec. 1987) vol. 23, No. 12, pp. 841-849.

T.L. Riss et al., *Rat Pituitary Tumor Cells in Serum-Free Culture. I. Selection of Thyroid Hormone-Responsive and Autonomous Cells*, In Vitro Cell Dev Biol (Feb. 1989) vol. 25, No. 2, pp. 127-135.

T.L. Riss et al., *Growth and Continuous Passage of COMMA-D Mouse Mammary Epithelial Cells in Hormonally Defined Serum-Free Medium*, Cancer Res. (Jul. 1987) vol. 47, No. 14, pp. 3776-3782.

T.L. Riss et al., *Human Recombinant Insulin-Like Growth Factor I. I. Development of a Serum-Free Medium for Clonal Density Assay of Growth Factors Using BALB/c 3T3 Mouse Embryo Fibroblasts*, In Vitro Cell Dev Biol (Nov. 1988) vol. 24, No. II, pp. 1099-1106.

M.C. Roque-Barreira et al., *Jacalin: an IgA-binding lectin*, J Immunol (Mar. 1985) vol. 134, No. 3, pp. 1740-1743, PMID 3871459 [PubMed—indexed for MEDLINE], Abstract, http://www.ncbi.nlm.nih.gov/enrez/query.fcgi?cmd=Retrieve&db=PubMed &list_uids=3871459&... printed on Feb. 21, 2003, 1 page.

M.C. Roque-Barreira et al., *IgA-affinity purification and characterization of the lectin jacalin*, Braz J Med Biol Res. (1986) vol. 19, No. 2, pp. 149-157.

W. Rosner et al., *Isolation and Characterization of the Testosterone-Estradiol-Binding Globulin From Human Plasma. Use of a Novel Affinity Column*, Biochemistry (Nov. 1975) vol. 14, No. 22, pp. 4813-4820.

W. Rosner, *The Functions of Corticosteroid-Binding Globulin and Sex Hormone-Binding Globulin: Recent Advances*, Endocr Rev (Feb. 1990) vol. 11, No. 1, pp. 80-91.

W. Rosner et al., *Testosterone-Estradiol-Binding Globulin of Human Plasma: Denaturation and Protection*, Biochim Biophys Acta (May 1974) vol. 351, No. 1, pp. 92-98.

J. Russo et al., *DNA Labeling Index and Structure of the Rat Mammary Gland as Determinants of its Susceptibility to Carcinogenesis*, J Natl. Cancer Inst. (Dec. 1978), vol. 61, No. 6, pp. 1451-1459.

I.H. Russo et al., *Developmental Stage of the Rat Mammary Gland as Determinant of its Susceptibility to 7,12-Dimethylbenz(a)anthracene*, J Natl. Cancer Inst. (Dec. 1978) vol. 61, No. 6, pp. 1439-1449.

M. Sabel et al., *Recent developments in breast imagining*, Phys Med Biol (Mar. 1996), vol. 41, No. 3, pp. 315-368, PMID 8778818 [PubMed—indexed for MEDLINE], Abstract, http://www.ncbi.nlm.nih.gov/enrez/query.fcgi?cmd=Retrieve&db=PubMed &list_uids=8778818&... printed on Feb. 21, 2003, 1 page.

R. Sager, *Expression genetics in cancer: shifting the focus from DNA to RNA*, Proc Natl. Acad. Sci USA (Feb. 1997), vol. 94, No. 3, pp. 952-959.

H.H. Samuels et al., *Depletion of L-3,5,3'-Triiodothyronine and L-Thyroxine in Euthyroid Calf Serum For Use In Cell Culture Studies of the Action of Thyroid Hormone*, Endocrinology (Jul. 1979) vol. 105, No. 1, pp. 80-85.

H. Sato et al., *Iron is deleterious to hormone-responsive pituitary cell growth in serum-free defined medium*, In Vitro Cell Dev Biol (Aug. 1991), vol. 27A, No. 8, pp. 599-602.

H. Sato et al., *Apotransferrins from several species promote thyroid hormone-dependent rat pituitary tumor cell growth in iron-restricted serum-free defined culture*, Mol Cell Endocrinol (Feb. 1992), vol. 83, Nos. 2-3, pp. 239-251.

R.W. Schatz et al., *Effects of Interaction Between Estradiol-17 Beta and Progesterone on the Proliferation of Cloned Breast Tumor Cells (MCF-7 andT47D)*, J Cell Physiol (Sep. 1985) vol. 124, No. 3, pp. 386-390.

A. Segaloff, *Hormone Therapy of Breast Cancer*, Banbury Report; 8 (1981), pp. 229-236.

J. Seidenfeld et al., *Single-Therapy Androgen Suppression in Men With Advanced Prostate Cancer: A Systematic Review and Meta-Analysis*, Ann Intern Med (Apr. 2000) vol. 132, No. 7, pp. 566-577.

G.B. Silberstein et al., *Regulation of Mammary Morphogenesis: Evidence for Extracellular Matrix-Mediated Inhibition of Ductal Budding by Transforming Growth Factor-Beta I*, Dev Biol (Aug. 1992), vol. 152, No. 2, pp. 354-362.

G.B. Silberstein et al., *Reversible Inhibition of Mammary Gland Growth by Transforming Growth Factor-Beta*, Science (Jul. 1987) vol. 237, No. 4812, pp. 291-293.

D.A. Sirbasku, *Hormone-Responsive Growth In Vivo of a Tissue Culture Cell Line Established From The MT-W9A Rat Mammary Tumor*, Cancer Res. (Apr. 1978) vol. 38, No. 4, pp. 1154-1165.

D.A. Sirbasku et al., *Thyroid Hormone and Apotransferrin Regulation of Growth Hormone Secretion by GHI Rat Pituitary Tumor Cells In Iron Restricted Serum-Free Defined Medium*, In Vitro Cell Dev Biol (Jan. 1992), vol. 28A, No. 1, pp. 67-71.

D.A. Sirbasku et al., *Thyroid Hormone Regulation of Rat Pituitary Tumor Cell Growth: A New Role for Apotransferrin As An Autocrine Thyromedin*, Mol Cell Endocrinol (May 1991) vol. 77, Nos. 1-3, pp. C47-C55.

D.A. Sirbasku et al., *Purification of an Equine Apotransferrin Variant (Thyromedin) Essential for Thyroid Hormone Dependent Growth of GHI Rat Pituitary Tumor Cells In Chemically Defined Culture*, Biochemistry (Jan. 1991) vol. 30, No. 1, pp. 295-304.

D.A. Sirbasku et al., *Control of Cell Growth. IV. Growth Properties of a New Cell Line Established From An Estrogen-Dependent Kidney Tumor of the Syrian Hamster*, Endocrinology (May 1976) vol. 98, No. 5, pp. 1260-1272.

D.A. Sirbasku et al., *Thyroid Hormone Dependent Pituitary Tumor Cell Growth in Serum-Free Chemically Defined Culture. A New Regulatory Role for Apotransferrin*, Biochemistry (Jul. 1991) vol. 30, No. 30, pp. 7466-7477.

D.A. Sirbasku et al., *Survey of the Mechanisms Regulating Estrogen Promoted Breast Cancer Cell Growth*, DOD Breast Cancer Research (Jun. 2000) Era of Hope, Proceedings vol. II, 2 pages.

D.A. Sirbasku, *Estrogen induction of growth factors specific for hormone-responsive mammary, pituitary, and kidney tumor cells*, Proc Natl. Acad. Sci USA (Aug. 1978) vol. 75, No. 8, pp. 3786-3790.

D.A. Sirbasku et al., *Estrogen mitogenic action. Ii. Negative regulation of the steroid hormone-responsive growth of cell lines derived from human and rodent target tissue tumors and conceptual implications*, In Vitro Cell Dev Biol Anim (Jul.-Aug. 2000) vol. 36 No. 7, pp. 428-446.

D.A. Sirbasku, *New Concepts in Control of Estrogen-Responsive Tumor Growth*, Banbury Report; 8 (1981), pp. 405-443.

E.P. Smith et al., *Estrogen Resistance Caused By A Mutation In The Estrogen-Receptor Gene In A Man*, N. Engl J Med (Oct. 1994) vol. 331, No, 16, pp. 1056-1061.

R.L. Smith et al., *Separation of plasma fibronectin from associated hemagglutinating acivity by elution from gelatin-agarose at pH 5.5*, Thromb Res. (Jan. 1985), vol. 37, No. 1, pp. 91-101, PMID 3983905 [PubMed—indexed for MEDLINE], Abstract, http://www.ncbi.nlm.nih.gov/enrez/query.fcgi?cmd=Retrieve&db=PubMed &list_uids=3983905&... printed on Feb. 20, 2003, 1 page.

M.J. Smyth et al., *A fresh look at tumor immunosurveillance and immunotherapy*, Nat Immunol (Apr. 2001) vol. 2, No. 4, pp. 293-299.

C. Sonneschein et al., *Somatic Mutation Theory of Carcinogenesis: Why It Should Be Dropped and Replaced*, Molecular Carcinogenesis (Dec. 2000) vol. 29, No. 4, pp. 205-211.

C. Sonneschein et al., *Human Serum Albumin Shares the Properties of Estrocolyone-I, The Inhibitor of the Proliferation of Estrogen-Target Cells*, J Steroid Biochem Mol Biol (Oct. 1996) vol. 59, No. 2, pp. 147-154.

A.M. Soto et al., *Cell proliferation of estrogen-sensitive cells: the case for negative control*, Endoc Rev (Feb. 1987), vol. 8, No. 1, pp. 44-52.

A.M. Soto et al., *The role of estrogens on the proliferation of human breast tumor cells*, J Steroid Biochem (Jul. 1985) vol. 23, No. 1, pp. 87-94, PMID 4021494 [PubMed—indexed for MEDLINE], Abstract, http://www.ncbi.nlm.nih.gov/enrez/query.fcgi?cmd=Retrieve&db=_PubMed&list_uids=4021494&... printed on Feb. 20, 2003, 1 page.

A.M. Soto et al., *Estrogen-Sensitive Proliferation pattern of Cloned Syrian Hamster Kidney Tumor Cells*, Cancer Res. (Jul. 1988), vol. 48, No. 13, pp. 3676-3680, PMID 3288332 [PubMed—indexed for MEDLINE], Abstract, http://www.ncbi.nlm.nih.gov/enrez/query.fcgi?cmd=Retrieve&db=_PubMed&list_uids=3288332&... printed on Feb. 20, 2003, 1 page.

A.M. Soto et al., *Control of Cell Proliferation: Evidence for Negative Control on Estrogen-Sensitive T47D Human Breast Cancer Cells*, Cancer Res. (May 1986) vol. 46, No. 5, pp. 2271-2275.

A.M. Soto et al., *A Plasma-Borne Specific Inhibitor of the Proliferation of Human Estrogen-Sensitive Breast Tumor Cells (Estrocolyone-I)*, J. Steroid Biochem Mol Biol (Dec. 1992) vol. 43, No. 7, pp. 703-712.

H.D. Soule et al., *A human cell line from apleural effusion derived from a breast carcinoma*, J Natl. Cancer Inst. (Nov. 1973) vol. 51, No. 5, pp. 409-416, PMID 4357757 [PubMed—indexed for MEDLINE], Abstract, http://www.ncbi.nlm.nih.gov/enrez/query.fcgi?cmd=Retrieve&db=_PubMed&list_uids=4357757&... printed on Feb. 19, 2003, 1 page.

H.L. Spiegelberg, *Biological activities of immunoglobulins of different classes and subclasses*, Adv Immunol (1974) vol. 19, pp. 259-294, PMID 4611172 [PubMed—indexed for MEDLINE], Abstract, http://www.ncbi.nlm.nih.gov/enrez/query.fcgi?cmd=Retrieve&db=_PubMed&list_uids=4611172&... printed on Feb. 15, 2003, 1 page.

J.E. Stern et al., *Secretory immune system of the male reproductive tract: effects of dihydrotestosterone and estradiol on IgA and secretory component levels*, J Reprod Immunol (Jun. 1992) vol. 22, No. 1, pp. 73-85, PMID 1522564 [PubMed—indexed for MEDLINE], Abstract, http://www.ncbi.nlm.nih.gov/enrez/query.fcgi?cmd=Retrieve&db=_PubMed&list_uids=1522564&... printed on Feb. 22, 2003, 1 page.

J.E. Stern et al., *Secretory component in breast cancer. Analysis of the levels in primary and metastatic disease*, Cancer Immunol. Immunother. (1985) vol. 19, No. 2, pp. 226-230, PMID 3847292 [PubMed—indexed for MEDLINE], Abstract, http://www.ncbi.nlm.nih.gov/enrez/query.fcgi?cmd=Retrieve&db=PubMed&list_uids=3847292&... printed on Feb. 21, 2003, 1 page.

K.R. Stone et al., *Isolation of a Human Prostate Carcinoma Cell Line (DU 145)*, Int. J. Cancer (Mar. 1978), vol. 21, No. 3, pp. 274-281.

J.S. Strobl et al., *Prolonged Retention of Estadiol by Human Breast Cancer Cells in Tissue Culture*, Cancer Res. (Sep. 1979) vol. 39, No. 9, pp. 3319-3327.

R.L. Sutherland et al., *High-Affinity Anti-Oestrogen Binding Site Distinct From The Oestrogen Receptor*, Nature (Nov. 1980) vol. 288, No. 5788, pp. 273-275, PMID 7432524 [PubMed—indexed for Medline], Abstract, http://www.ncbi.nlm.nih.gov/enrez/query.fcgi?cmd=Retrieve&db=_PubMed&list_uids=7432524&... printed on Feb. 20, 2003, 1 page.

M. Swift, *Public health Burden of Cancer in Ataxia-Telangiectasia Heterozygotes*, J. Natl. Cancer Inst (Jan. 2001), vol. 92, No. 2, pp. 84-85.

M. Tanji et al., *A Steroid-Binding Protein Mediates Estrogen-Dependent Inhibition of Growth of MCF-7 Breast Cancer Cells*, Anticancer Res. (Jul.-Aug. 2000) vol. 20, No. 4, pp. 2785-2789.

M. Tanji et al., *Growth Inhibition of MCF-7 Cells by Estrogen Is Dependent Upon a Serum Factor*, Anticancer Res. (Jul.-Aug. 2000) vol. 20, No. 4, pp. 2779-2783.

A.H. Tashjian, *Clonal Strains of Hormone-Producing Pituitary Cells*, Methods Enymol (1979) vol. 58, pp. 527-535.

S.V. Tavtigian et al., *The Complete BRCA2 Gene and Mutations in Chromosome 13q-Linked Kindreds*, Nat. Genet (Mar. 1996) vol. 12, No. 3, pp. 333-337, PMID 8589730 [PubMed—indexed for MEDLINE], Abstract, http://www.ncbi.nlm.nih.gov/enrez/query.fcgi?cmd=Retrieve&db=_PubMed&list_uids=8589730&... printed on Feb. 15, 2003, 1 page.

M.J. Tsai et al., *Molecular mechanisms of action of steroid/thyroid receptor superfamily members*, Annu. Rev. Biochem (1994) vol. 63, pp. 451-486, PMID 7979245 [PubMed—indexed for MEDLINE], Abstract, http://www.ncbi.nlm.nih.gov/enrez/query.fcgi?cmd=Retrieve&db=_PubMed&list_uids=7979245&... printed on Feb. 21, 2003, 1 page.

J.P. Vaerman et al., *Antibody against the human J chain inhibits polymeric Ig receptor-mediacted biliary and epithelial transport of human polymeric IgA*, Eur. J. Immunol. (Jan. 1998) vol. 28, pp. 171-182.

S. Valtanen et al., *Poliovirus-Specific Intestinal Antibody Responses Coincide With Decline of Poliovirus Excretion*, J. Infect. Dis. (Jul. 2000) vol. 182, pp. 1-5.

J. Veldscholte et al., *A mutation in the ligand binding domain of the androgen receptor of human LNCaP cells affects steroid binding characteristics and response to anti-androgens*, Biochem Biophys Res. Commun (Dec. 1990) vol. 173, No. 2, pp. 534-540.

J. Veldscholte et al., *Unusual specificity of the androgen receptor in the human prostate tumor cell line LNCaP: high affinity for progestagenic and estrogenic steroids*, Biochim Biophys Acta (Apr. 1990) vol. 105, pp. 187-194.

F. Vignon et al., *Effects of Plasma Estrogen Sulfates in Mammary Cancer Cells*, Endocrinology (Apr. 1980) vol. 106, No. 4, pp. 1079-1086.

F. Vignon et al., *Antiestrogens inhibit the mitogenic effect of growth factors on breast cancer cells in the total absence of estrogens*, Biochem Biophys Res. Commun (Aug. 1987) vol. 146, No. 3, pp. 1502-1508, PMID 3304294 [PubMed—indexed for MEDLINE], Abstract, http://www.ncbi.nlm.nih.gov/enrez/query.fcgi?cmd=Retrieve&db=_PubMed&list_uids=&3304294... printed on Feb. 20, 2003, 1 page.

J.F. Viret et al., *Mucosal and systemic immune responses in humans after primary and booster immunizations with orally administered invasive and noninvasive live attenuated bacteria*, Infect Immun (Jul. 1999) vol. 67, No. 7, pp. 3680-3685.

I Vorechovsky et al., *the ATM gene and susceptibility to breast cancer: analysis of 38 breast tumors reveals no evidence for mutation*, Cancer Res. (Jun. 1996) vol. 56, No. 12, pp. 2726-2732, PMID 8665503 [PubMed—indexed for MEDLINE], Abstract, http://www.ncbi.nlm.nih.gov/enrez/query.fcgi?cmd=Retrieve&db=PubMed&list_uids=8665503&... printed on Feb. 21, 2003, 1 page.

Y. Wang et al., *Identification of a dominant negative form of the human estrogen receptor*, Mol. Endocrinol (Nov. 1991) vol. 5, No. 11, pp. 1707-1715, PMID 1779972 [PubMed—indexed for MEDLINE], Abstract, http://www.ncbi.nlm.nih.gov/enrez/query.fcgi?cmd=Retrieve&db=_PubMed&list_uids=1779972&... printed on Feb. 20, 2003, 1 page.

C.W. Welsch, *Host Factors Affecting the Growth of Carcinogen-induced Rat Mammary Carcinomas: A Review and Tribute to Charles Brenton Huggin*, Cancer Res. (Aug. 1985) vol. 45, No. 8, pp. 3415-3443.

R.V. Wenn et al., *Distribution of Testosterone-Estradiol Binding Globulin (TeBG) In The Higher Vertebrates*, Endokrinologie (Jul. 1977) vol. 69, No. 2, pp. 151-156.

T.E. Wiese et al., *Optimization of estrogen growth response in MCF-7 cells*, In Vitro Cell Dev Biol (Sep.-Oct. 1992) vol. 28A, No. 9-10, pp. 595-602.

R. Wooster et al., *Identification of the breast cancer susceptibility gene BRCA2*, Nature (Dec. 1995) vol. 378, No. 6559, pp. 789-792, PMID 8524414 [PubMed—indexed for MEDLINE], Abstract, http://www.ncbi.nlm.nih.gov/enrez/query.fcgi?cmd=Retrieve&db=_PubMed&list_uids=8524414&... printed on Feb. 15, 2003, 1 page.

J. Yang et al., *Estrogen receptor variants in epithelial compartment of normal human breast*, Endocrine (Jun. 2000), vol. 12, No. 3, pp. 243-247, PMID 10963044 [PubMed—indexed for MEDLINE], Abstract, http://www.ncbi.nlm.nih.gov/enrez/query.fcgi?cmd=Retrieve&db=_PubMed&list_uids=10963044&... printed on Feb. 12, 2003, 1 page.

K.R. Yamamoto, *Steroid receptor regulated transcription of specific genes and gene networks*, Annu Rev Genet (1985) vol. 19, pp. 209-252, PMID 3909942 [PubMed—indexed for MEDLINE], Abstract, http://www.ncbi.nlm.nih.gov/enrez/query.fcgi?cmd=Retrieve&db=_PubMed&list_uids=3909942&... printed on Feb. 21, 2003, 1 page.

D.A. Zajchowski et al., *Estrogen inhibits the growth of estrogen receptor-negative, but not estrogen receptor-positive, human mammary epithelial cells expressing a recombination estrogen receptor*, Cancer Res. (Oct. 1993) vol. 53, No. 20, pp. 5004-5011, PMID 8402691 [PubMed—indexed for MEDLINE], Abstract, http://www.ncbi.nlm.nih.gov/enrez/query.fcgi?cmd=Retrieve&db=_PubMed&list_uids=8402691&... printed on Feb. 21, 2003, 1 page.

PCT International Search Report, PCT/US02/36632 dated Jul. 28, 2003 (1 p.).

PCT International Search Report, PCT/US02/36542 dated Oct. 23, 2003 (2 p.).

Krajci et al., The human transmembrane secretory component (poly-Ig receptor): molecular cloning, restriction fragment length polymorphism and chromosomal sublocalization. Human Genetics. 1991, vol. 87, pp. 642-648.

* cited by examiner

SCREENING METHOD FOR PREDICTING SUSCEPTIBILITY TO BREAST CANCER

CROSS-REFERENCE TO RELATED APPLICATIONS

This application claims the benefit under 35 U.S.C. §119(e) of U.S. Provisional Patent Application No. 60/332,920 filed Nov. 14, 2001, and is a continuation-in-part of U.S. patent application Ser. Nos. 09/852,958 and 09/852,547, both filed May 10, 2001, the disclosures of each of which are hereby incorporated herein by reference.

STATEMENT REGARDING FEDERALLY SPONSORED RESEARCH OR DEVELOPMENT

Research leading to the present invention was supported in part by the federal government under Grant Nos. DAMD17-94-J-4473, DAMD17-98-1-8337 and DAMD17-99-1-9405 awarded by the Defense Department through the US Army Medical Research and Materiel Command, Breast Cancer Research Program. The United States government may have certain rights in the invention.

BACKGROUND OF THE INVENTION

1. Field of the Invention

The present invention generally relates to genetic changes associated with the onset of sporadic breast cancer, and more particularly to methods and compositions for identifying such changes and for screening women at risk of developing the disease.

2. Description of Related Art

The number of breast cancer cases diagnosed each year worldwide is about one million (1). Breast cancer represents 18% of all cancers in women and, with the exception of skin cancer, is the most common site of cancer in women. In decreasing order, the incidence of other cancers in women are cervix, colon/rectum, stomach, endometrium, lung, ovary, mouth/pharynx, esophagus and lymphoma (1). The fact that a similar pattern is widespread throughout the Western world suggests that related genetic changes may be the origin of cancer development at these sites.

Many risk factors have been defined for breast cancer (1-10). When specific risks are given relative ranks, an interesting pattern emerges. The major four risk factors are age (relative risk 10) followed by geographic location, previous breast cancer, and previous benign breast disease (relative risks of 4 to 5) (1). Reproductive history is next most important with relative risks of 2 to 3 (1). Other factors such as diet, alcohol consumption, socioeconomic group and family history are in the relative risk range of 1.3 to 2 (1). Notably, the risk of oral contraceptives or hormone replacement therapy is low, in the relative range of 1.2 to 1.4 (1). From these data, it can be concluded that the origin of breast cancer, and hence the number of causative genes, are yet to be identified. While modification of personal habits, reproductive considerations, and behavior can reduce risk, the benefits are modest and certainly offer no guarantees. Thus far, traditional epidemiology has not provided "the" origin of breast cancer. Indeed, based on epidemiological data, it has even been suggested that breast cancer arises from a single cause (11). But this conclusion came with the statement that the cause was still unknown. With the growing importance of genetic analysis, it now appears likely that epidemiology will move into this arena to make further advances.

Other investigators have made observations that are critical to understanding the genetic origins of breast cancer. First, it is clear that only a small minority of cancers originate from germ-line mutations (12). Second, there are more than 100 changes in gene expression detectable in breast cancer cells versus normal breast epithelium (12). This large number promises to increase to 200 to 300 with new technology (13,14). Based on a recent discussion (12), cancer mutations have been defined as Class I, which involve changes in gene DNA sequences, and Class II genetic alterations, in which changes in gene expression are detected by mRNA analysis (12). By selecting specific RNA species for further study, information can be gained, but there is no assurance which change(s) is causative. Indeed, it seems highly unlikely that cancer development requires this huge number of gene alterations. It is more likely that most of the changes are the result of malignant transformation, not the cause. It may be possible to use mass gene expression analysis (e.g. microarray technology) to predict breast cancer risk or susceptibility, but for now this seems distant.

It seems reasonable to retreat from these types of "shot-gun" analysis and approach the issue from another perspective. In this proposal, focus is placed on genetic changes that are more subtle and are represented by loss of heterozygosity (LOH) or other allelic imbalances (AI). These genetic alterations are known to be associated with a high risk of cancer development. There are categories of women with three or more times higher risk of developing breast cancer than average. They are often classified into a group termed "familial breast cancer". They have (i) a first degree relative with breast or ovarian cancer, (ii) one first degree relative with disease diagnosed under the age of 40, (iii) two first or second degree relatives with breast or ovarian cancer under the age of 60, or (iv) three first or second degree relatives with breast or ovarian cancer on the same side of the family (1). It is tempting to conclude that this represents an inherited trait or at least a propensity to development of the disease. This conclusion must be tempered however by an understanding that "inherited" might include as yet unrecognized non-biological inheritance such as culture inheritance and common environmental conditions (15). While genetic predisposition remains a strong possibility, it may not be of the type seem with BRCA1 (16) and BRCA2 (17) which are inherited as autosomal dominants from either parent, albeit with varying penetrance. Equally, it is possible that the predisposition is a recessive inheritance, also with varying penetrance, or a recessive mutation that leads to breast cancer development. It may also represent inherited or acquired genetic abnormalities such as loss of heterozygosity (LOH) or other allelic imbalances (AI) such as abnormal gene numbers.

A familial aspect to breast cancer has been recognized for some time. However, this term may have different meanings. It might indicate "familial clustering" which is the existence of several cases in an extended family. Because breast cancer will occur in 10% of women, chance alone will allow some familial clusters depending upon the number of females in a related group. Therefore, because a family has more than one member with the disease, it does not necessarily follow that there is a genetic cause. In contrast, the familial aspect of breast cancer might also indicate "familial aggregation" which is increased risk to close relatives of women with breast cancer compared to relatives of women without the disease. Familial aggregation is another matter. Its existence may depend on genetic and/or non-genetic causes. As discussed above, the presence of breast cancer in one or more first degree relatives increases risk significantly. As the number of breast cancers in first and second degree relatives increases, especially at younger ages, there is strong reason to hold that there are familial factors that may be genetic. If genetic in origin, identification of these genes will be a major advance in understanding breast cancer (18). Genes which show LOH or AI are strong candidates for identification. The composition and methods of identification of such genes is a primary focus of this disclosure.

The question is: "What genes are being sought to explain familial aggregation"? The low frequency of BRCA1 and BRCA2 does not support the view that they account for one million new cases each year worldwide (18). Although somewhat difficult to assess, one report indicates an estimated frequency of significant mutations in these two genes in the US and UK of 0.0005 to 0.002 (19). Another report (25) states mutations in 1 in 152 and 1 in 833 for mutations in these two genes. It is higher in some regions of the world such as Scandinavia and approaches 1 in 40 in Ashkenazi Jews (20). The major issues resulting from the lack of broad application of BRCA1 and BRCA2 are what other genes are to be sought and by what methods.

There are three separate genetic syndromes that are associated with above average rates of breast cancer development (26). These are Li-Fraumeni Syndrome, Cowden's Syndrome and Ataxia Telangiectasia (AT). Each appears to involve a different gene lesion or small set of lesions, but nonetheless all contribute to a higher risk of breast cancer. These syndromes illustrate the point that a small number of critical mutations are likely involved in breast cancer development. In addition, Lynch Syndrome II is associated with breast cancer development (28). The genetic lesion is important in Lynch Syndrome because it involves impairment of the critical process of DNA mismatch repair (29,30).

Li-Fraumeni Syndrome (LFS) is a very rare germ-line mutation in p53 (31) that increases premenopausal breast cancer as well as sarcomas, brain tumors, leukemia and adrenocortical cancer (32,33). LFS is an autosomal dominant syndrome for which genetic testing is not yet available. It is thought that availability would not change medical management (34). Nonetheless, p53 mutations occur in 30% of sporadic breast cancers (27). The very diverse types of p53 mutations in breast cancer pose a problem for genetic testing (27). One study suggests that mutations at codon 248 might be associated with higher breast cancer risks (35). While screening for P53 changes alone may not be productive, combination screening of P53 with other genes may be very informative based on the accepted view that cancer development is a multistep process involving a relatively few genes.

Cowden's Syndrome is characterized by excess breast cancer, gastrointestinal malignancies, thyroid disease, and other benign conditions (36). Cowden's syndrome carries a lifetime breast cancer risk of 25 to 50%. There is usually early onset and often appearance of bilateral disease (37). There is a germ-line mutation in PTEN, a protein tyrosine phosphatase with homology to tensin. PTEN acts as a tumor suppressor and functions in the control of the cell cycle (38). As with P53, screening for PTEN mutations alone may not be informative, but in combination with other genes, may provide important prognostic value.

Ataxia Telangiectasia (AT) is an autosomal recessive disorder characterized by neurologic deterioration, telangiectasias, immunodeficiencies, and marked hypersensitivity to ionizing radiation. Approximately 1% of the population may be heterozygote carriers of the AT mutation (ATM). Over 200 mutations have been identified in the ATM. The majority are truncations (39). ATM proteins have a role in cell cycle control (40). ATM individuals are susceptible to cancer. Studies have shown that even heterozygotes are at elevated risk for breast cancer (41,42). This is the case despite the fact that the ATM is not identified in breast cancer specimens in excess of its occurrence in control populations (43-45). The link between ATM and breast cancer may be related to the kinase coded for by the AT gene. Its absence leads to chromosomal instability, a condition often associated with breast cancer. Because of the relative high frequency of heterozygotes in the U.S. and European populations, analysis of the AT gene plus other genes will be useful.

Lynch Syndrome II is a form of several related diseases first reported as "cancer family syndrome" (46). Other types of this disease are Lynch Syndrome I, (also called hereditary nonpolyposis colon cancer—HNPCC), Miur's Syndrome (also called Torre's Syndrome), Down family Syndrome, Bloom's Syndrome and finally Dyskeratosis congenital (46). For the purposes of example, Lynch Syndrome II will be discussed. This discussion is intended to encompass these other related forms of the disease as they relate to breast cancer development. Lynch Syndrome II is accompanied by the aggregation of colon, endometrial, ovarian and breast cancer in families (28). This disease is due to mutations in DNA mismatch repair genes designated hMSH2 and hMLH1 (47). The result of these mutations is to create microsatellite instability (48). Microsatellite instability is used today to measure the mutations in populations of specimens from colon cancer patients (49). This has given a range of estimates of the size of population bearing these mutations. It seems likely that the two mutations lead to the accumulation of mutations throughout the genome. With time, genes important in growth regulation of mucosal cells become altered and result in the onset of cancer.

Cancer is now generally thought to be a multistep disease that arises in response to genetic changes altering key regulatory proteins within the cells. The mutations leading to cancer can be present in the germ line or can arise as somatic mutations in the tissues. It is clear that a progression exists whereby normal cells change to arrive at the fully malignant state capable of metastasizing to distant body sites. While many gene expression changes can be detected by sophisticated technology, it is reasonable to conclude that the powerful methods applied mask the fact that only a relative few changes ultimately result in cancer.

Although advancement has been made toward understanding genetic predisposition to development of certain breast cancers, there remains a pressing need for ways to identify the genetic changes associated with the onset of sporadic breast cancers, which represent about 6070% of the total number of cases diagnosed each year that have no known genetic origin. There is also a great need for ways to screen individuals for risk of developing the disease and for taking appropriate preventative measures.

SUMMARY OF PREFERRED EMBODIMENTS

The present invention addresses the problem of sporadic breast cancer, which represents about 60 to 70% of the total cases diagnosed each year and has no known genetic origin. New methods and compositions are provided which employ a newly identified Poly-Ig (Fc) receptor or a Poly-Ig-like (Fc) receptor that is characterized by, among other things, its ability to mediate the recently discovered cell growth inhibitory function of the secretory immune system (e.g., dimeric/polymeric IgA and polymeric IgM). These discoveries are described in detail in U.S. patent application Ser. Nos. 09/852,547 and 09/852,958, and in International Patent Application Nos. PCT/US01/15171 and PCT/US01/15183, the disclosures of which are hereby incorporated herein by reference.

In accordance with certain embodiments, methods and compositions for carrying out genetic analysis of the Poly-Ig (Fc) receptor or a Poly-Ig-like (Fc) receptor to determine breast cancer susceptibility in heterozygotes and homozygotes are provided. In some embodiments of the present invention, gene screening compositions and methods are provided for identifying women at risk of developing the disease either through a familial pattern or a sporadic pattern. In some embodiments, methods and compositions for double screening an individual for Poly-Ig (Fc) receptor or Poly-Ig-like (Fc) receptor mutations and for mutations of other breast cancer predisposing genes are provided. In certain embodiments of the invention, methods and compositions for screening an individual for heterozygous ATM mutations are provided which include comparing the results to screening results for mutations in the Poly-Ig (Fc) receptor or Poly-Ig-like (Fc) receptor.

In some embodiments, methods and compositions for screening breast cancer specimens for mutations in growth regulating genes are provided. In another embodiment of the present invention, methods and compositions for evaluating breast fluid derived cells for molecular changes in predetermined genes. In some embodiments, premalignant changes in the Poly-Ig (Fc) receptor or a Poly-Ig-like (Fc) receptor gene are assessed, and changes in other predetermined breast cancer predisposing genes are also evaluated.

Also provided in accordance with the present invention is an analytic method that permits a determination of breast cancer susceptibility or risk of future disease. The method includes genetic testing for loss of heterozygosity (LOH) and other Allelic Imbalances (AI) in the D1S58 locus of chromosome 1. In some embodiments, the analysis is done with blood cells or mucosal scraping cells to test for germline alterations. For example, analyses are carried out with samples from young women or those at risk because of first or second degree relative breast cancer patterns. Performing early genetic analysis is highly desirable for identifying women at risk. If germline mutations are found or if somatic mutations are found, an appropriate "risk reduction" or "prevention" technology as described in U.S. patent application Ser. No. 09/852,547 and in International Patent Application No. PCT/US01/15171 (also identified as item 21 in the References, below), or in co-pending U.S. patent application Ser. No. 11/946,190, entitled "Breast Cancer Eradication Program," can be timely applied. Additional preventative or risk reduction methods and compositions are described in co-pending U.S. patent application Ser. No. 10/293,439, entitled "Anti-estrogen and Immune Modulator Combinations for Treating Breast Cancer."

In other embodiments, similar analyses are done with breast fluid derived cells to identify somatic mutations. In this way somatic changes are revealed that may be classified as "pre-malignant" and hence useful in identifying risk in the relative near future. In other embodiments, genetic analysis of breast tumors are carried out as an aid to determining the type of cancer present and indicating if immune therapy is appropriate.

In still other embodiments, a method of treating an individual identified as heterozygous or homozygous for a mutation in a gene coding for a Poly-Ig (Fc) receptor or a Poly-Ig-like (Fc) receptor capable of mediating estrogen reversible inhibition of breast cancer cell growth by an immunoglobulin inhibitor is provided. After an at-risk individual is identified, using the an above-described screening method, treatment includes enhancing the amount of immunoglobulin inhibitor ("immune modulator"), or an immune modulator mimicking compound, contacting a mucosal epithelial tissue of said individual. This can be done by either boosting the body's natural secretory immune system (e.g. by way of an immune enhancing agent such as, Levimisol, Imiquimod, Picibanil and DHEA) or by administering a pharmaceutical composition containing active forms of the immunoglobulin inhibitors or a drug that mimics its inhibitory activity. In some embodiments, an anti-estrogen compound, such as tamoxifen, for example, is also administered to the individual. In some embodiments a hormone is co-administered with an anti-estrogen or immune modulator to reduce side effects of the drug. In some embodiments an aromatase inhibitor is also administered to the individual. In some embodiments the treatment also includes prophylactic surgical removal of non-cancerous breast tissue.

These and other embodiments, features and advantages of the present invention will become apparent with reference to the following description.

DETAILED DESCRIPTION OF PREFERRED EMBODIMENTS

Recent discoveries disclosed in co-owned, co-pending U.S. patent application Ser. Nos. 09/852,547 and 09/852,958, and in International Patent Application Nos. PCT/US01/15171 and PCT/US01/15183 (also identified as items 21 and 22 in the References, below), each of which is hereby incorporated herein by reference, are expected to lead to resolution of the problem of how to identify genes that are key to the 60 to 70% of breast cancer cases that are today termed "sporadic." The isolation of new "serum factor(s)" that regulate estrogen responsive breast cancer cell growth in culture is described in the preceding applications. The purification yielded dimeric/polymeric immunoglobulin A (IgA) and pentameric immunoglobulin M (IgM) as the active regulators. These immunoglobulins ("immunoglobulin inhibitors") arrested estrogen target tumor cell growth completely at low nanomolar concentrations, and their inhibitory effects were entirely reversible by picomolar concentrations of estrogens. That disclosure revealed a previously unknown function for the secretory immune system. In the above-identified patent applications, a major role for TGFβ in breast growth regulation is also identified: it is a cytokine that controls IgA/IgM immunocytes. Breast cancer growth is best defined as negative paracrine control by secretory immunoglobulins (immunoglobulin inhibitors) and positive direct control by estrogens. In conjunction with this work, the longstanding problem of the regulation of estrogen dependent cell growth in culture under serum-free defined medium conditions was solved. These results have great physiological relevance. IgA and IgM are secreted by B immunocytes located in the lamina propria of estrogen target tissues including breast. They are more than 90% of the immunoglobulins secreted into breast milk. The positioning of the immunocytes in the tissue adjacent to the epithelial cells and the secretion of the immunoglobulins is hormone regulated.

It was found that the secretory immune system products immunoglobulins A and M (IgA and IgM) inhibit the growth of estrogen-sensitive (early) breast cancer by suppressing cell replication. This is the first time a connection was established between the secretory immune system and early estrogen receptor positive (ER$^+$) breast cancer growth. In addition, when breast cancer becomes most malignant (i.e. ER$^-$ hormone-insensitive stages), control by immune system IgA and IgM is lost. Evidence points to the Poly-Ig receptor or a very similar Poly-Ig-like Fc receptor as the mediator of the inhibitory effects of IgA and IgM. This receptor may be the long sought after gene that explains many of the "sporadic" breast cancers. Here, the term "sporadic" refers to breast cancer originating from unknown genetic origins. The Poly-Ig receptor gene is located at locus D1S58 on chromosome 1 (23) which has been proven to be a "hot spot" for allelic imbalances in more than 70% of breast cancers (24). A hot spot is a chromosomal loci or gene that is frequently altered in breast cancer specimens. This site has 46% loss of heterozygosity (LOH) in breast cancer specimens (24) and 30% incidence of allelic imbalance (AI) (24). This research, and that described in the above-identified U.S. and PCT patent applications (21,22), support the conclusion that this gene will have notably broader significance in "sporadic" breast cancer etiology than BRCA1 (located on chromosome 17) or BRCA2 (located on chromosome 13).

Mutations in genes that are critical to cell growth or are known to be predisposing for breast cancer have been described. Such mutations can either cause activation of oncogenes to promote cell replication or cause inactivation of suppressors to release cells to growth without control. In studies related to the present disclosure and described in the above-identified U.S. and PCT patent applications, the Poly-Ig (Fc) receptor or a similar Poly-Ig-like (Fc) receptor has been identified as a tumor suppressor. Binding the ligands IgA or IgM results in growth arrest in ER$^+$ breast cancer cells. When this receptor is absent, cells replicate without immune control. The gene identified in this invention has not previously been recognized to have growth regulating properties. As this study developed the application of this new receptor gene function indicated an important concern for both germ line and somatic mutations.

Although the majority of cancers are thought to arise by somatic mutation, the fact that "familial aggregation" of breast cancers exists is strong evidence in favor of germ line analysis. The line of thought is to study both types of mutations in the poly-Ig-like receptor. Germ line mutations will be sought with blood cells or mucosal cells (i.e. mucosal scrapings) obtained from women. Somatic mutations are revealed via examination of breast cancer specimens and cells aspirated from breast ducts or in breast fluid samples.

Key models of germ line breast cancer predisposing genes are readily available from sources known to investigators in this field. These include TP53, ATM, PTEN, MLH1 and the MSH2 genes. If the full expression of these predisposing genes is to be realized, other mutations must contribute. The Poly-Ig-like receptor is found in every steroid and thyroid hormone responsive cell line examined to date. When the receptor is lost, cells achieve full autonomy. This indicates that the receptor gene may be a key contributor to the development of breast cancer as well as other cancers arising from mucosal tissues.

Example 1

Genetic Analysis of the Poly-Ig (Fc) Receptor or Poly-Ig-like (Fc) Receptor to Determine Breast Cancer Susceptibility in Heterozygotes and Homozygotes Individuals seeking to determine breast cancer risk for the reasons cited above will be screened for predisposing genetic damage/mutations in the gene for the Poly-Ig (Fc) receptor or Poly-Ig-like (Fc) receptor. This will be done using lymphocytes and technology suited to rapid but accurate screening (e.g. pyrosequencing and rapid PCR methodology). This analysis will be preformed similarly to those used to identify heterozygotes and homozygotes for the ATM mutation and for hereditary nonpolyposis colorectal cancer (HNCC). Studies done with control volunteers will be carried out to determine natural innocuous mutations in the gene and to determine if selected populations have different mutations and hence may be at greater risk. It is expected that one damaged gene will confer greater risk than controls because inactivation of the other functional gene will eliminate immune negative growth regulation by IgA and IgM. Suitable techniques that will be used for this genetic analysis are well known in the art. Such an analysis has not been recognized previously as useful in determining risk for breast cancer in populations before development of the disease. Individuals showing homozygous mutations are considered at highest risk and will be counseled to decide on surgical prophylactic measures or on the use of tamoxifen or other anti-estrogen as preventative measures. Thus, genetic screening can be used to not only to define potential risk, but to assistant in initiating preventative life saving actions, as discussed in more detail in the following example.

Example 2

Screening for Loss of Heterozygosity (LOH) or Allelic Imbalance (AI) in the Poly-Ig (Fe) Receptor or Poly-Ig-like (Fe) Receptor Using blood cells, mucosal scrapings, breast fluid derived cells and other body and tissue samples and fluids, the presence of LOH and AI in the Poly-Ig (Fc) receptor or a Poly-Ig-like (Fc) receptor gene will be determined by methods commonly applied and well known. Preferably the D1S58 locus of chromosome 1 will be a primary point of focus. This analysis can begin at very young ages (i.e. nine or ten years old ) or can be initiated at age 25 when breast cancer rates are still very low. Analysis of breast fluid cells can be continued with women showing LOH or AI at early ages. This information is used along with methods such as mammography to monitor women at high risk. Early genetic analysis, as described in this example and in Examples 1, 3 and 4, is especially valuable for identifying women at risk so that appropriate steps for risk reduction or prevention can be taken. If germline mutations are found or if somatic mutations are found, the issue then becomes "what to do?". Preventative and therapeutic compositions and methods are described in co-pending U.S. patent application Ser. No. 09/852,547 and in International Patent Application No. PCT/US01/15171 (also identified as item 21 in the References, below), or in co-pending U.S. patent application Ser. No. 10/293,019 entitled "Breast Cancer Eradication Program." Additional preventative and risk reduction methods and compositions are described co-pending in U.S. patent application Ser. No. 10/293,439 entitled "Anti-estrogen and Immune Modulator Combinations for Treating Breast Cancer." The disclosures of these co-owned patent applications are hereby incorporated herein by reference.

Example 3

Double Screening for Poly-Ig (Fc) Receptor or Poly-Ig-like (Fc) Receptor Mutations and Mutations in Other Breast Cancer Predisposing Genes Because the development of cancer most likely depends on more than one mutation (50), and may involve several cell types (50), it is useful to screen for mutations in genes that will lead to damage in other genes. Both the Lynch Syndrome II genes and the Cowden's disease gene are candidates for double screening along with the Poly-Ig (Fc) receptor or a Poly-Ig-like (Fe) receptor. For example, changes in the effectiveness of the Lynch Syndrome genes can lead to a gradual accumulation of mutations. If mutations are also present in the Poly-Ig-like receptor, risk can be expected to be substantially higher than controls. Heterozygotes for the Lynch Syndrome genes have not been previously analyzed to determine if they possess an increased risk of breast cancer. Likewise, heterozygotes for the Cowen's mutation have not been examined before to determine breast cancer susceptibility. These results will then be compared to results of screens for the Poly-Ig (Fe) receptor or Poly-Ig-like (Fe) receptor to identify those individuals at greatest risk. Suitable risk reduction or preventative measures can then be implemented, as discussed in the preceding Example.

Example 4

Screening for Heterozygous ATM Mutations and Comparison to Mutations in the Poly-Ig (Fc) Receptor or Poly-Ig-like Receptor The ATM mutation, associated with the disorder ataxia telangiectasia, is not found in breast cancers. Nonetheless, it is clear that even heterozyogotes are at substantial risk for breast cancer. In light of the present disclosure of the importance of breast cancer cell growth control by the secretory immunoglobulins, it is of particular significance that the AT disorder is known to be accompanied by chromosome fragility (i.e. lack of repair after ionizing radiation) and a marked deficiency in IgA. Because the ATM mutation is so widely distributed in the population, it is important to initiate a screening for this mutation as a first line defense against breast cancer. Identification of meaningful mutations will then permit decisions by women to elect preventative measures. Pending results indicating a potential problem, these same individuals will then be offered another screening for the Poly-Ig (Fc) receptor or a Poly-Ig-like (Fc) receptor as a further indicator of risk status. If significant mutations are found in one or both receptor genes, prophylactic or preventative measures can be initiated, as discussed above in Example 2.

Example 5

Screening of Breast Cancer Specimens for Mutations in Growth Regulating Genes

Specimens from breast cancer patients will be screened for alterations in the Poly-Ig (Fe) receptor or a Poly-Ig-like receptor to assist in therapy decisions and to identify individuals at greatest risk and requiring more intense intervention. This approach identifies somatic mutations. Conventional screening techniques will also be used to identify heterozygous genes including the Lynch Syndrome gene and the Cowden's disease gene as well as alterations in TP53. The molecular fingerprinting of tumors is expected to increase the effectiveness of treatment programs by allowing each to be adapted to the individual patient. Future use of molecular methods is expected to provide a genetic profile of a patient's primary tumor as well as to provide information relevant to family members concerning their potential risks.

Example 6

Evaluation of Breast Fluid Derived Cells for Molecular Changes in Genes

Cells will be obtained from breast fluids by any of a number of well known methods, or, alternatively, by newer methods that are known in the art and have been described in the literature for direct aspiration of the breast milk ducts. Commercial milk pumps are available for this application. Premalignant changes in the Poly-Ig (Fc) receptor or a Poly-Ig-like (Fc) receptor gene will be evaluated as will be changes in the other breast cancer predisposing genes discussed above. This technology is expected to identify somatic mutations at the site of breast cancer development. Identification of sets of changes consistent with long-term development of the disease will permit immediate intervention to eradicate the altered cells or arrest the mutation process.

After parturition, cells will be harvested from expressed breast milk and evaluated for somatic mutations. This analysis can be readily carried out during routine postpartum doctor's office visits. The cells will be collected directly on to filters (supplied) and DNA screening conducted, as previously described. This method permits direct assessment of the genetic status of a subset of reproductive age women without disruption of daily routines. Fluid aspiration can also be done during routine mammography examinations. Nipple pumps, which are available from well known commercial suppliers, can be used to withdraw only the few milliliters of fluid required.

Once a person or a group of persons have been identified as being at risk for breast cancer using one or more of the foregoing procedures, a program of prevention or risk reduction can be implemented, as described in, for example, copending U.S. patent application Ser. No. 11/946,190 entitled "Breast Cancer Eradication Program," and U.S. patent application Ser. No. 10/293,439 entitled "Anti-estrogen and Immune Modulator Combinations for Treating Breast Cancer." The disclosures of these co-owned patent applications are hereby incorporated herein by reference. Such program can include (a) enhancing the amount of an immunoglobulin inhibitor ("immune modulator") of cancer cell growth that contacts the breast ductal tissue of said individuals; and/or administering an immunoglobulin inhibitor mimicking compound; administering an anti-estrogenic compound; (b) administering an aromatase inhibitor; (c) enhancing the number of B immunocytes producing IgA or IgM in breast tissue; and/or (d) immunizing individuals at risk of developing breast cancer against microorganisms known to or suspected of causing breast cancer. Some immunoglobulin inhibitor mimicking compounds that may be used include: Tamoxifen and MER-25 and chemically substituted or modified derivatives thereof. To reduce possible side effects of MER-25, or its derivative compound, in some cases it may also be desirable to co-administer progesterone or another hormone. Some immune enhancers that may be used include: Levimisole, Imiquimod, Picibanil, and DHEA. Some useful anti-estrogens include: Tamoxifen, Toremifene, ICI 16384, ICI 182780, EM-800, RU 58688 and EM-139.

REFERENCES (1) McPherson K, Steel C M & Dixon J M (2000) Breast cancer—epidemiology, risk factors and genetics. BMJ 321:624-628.

(2) Alberg A J Helzlsouer K J (1997) Epidemiology, prevention, and early detection of breast cancer. Current Opinion Oncology 9:505-511.

(3) Kelsey J L & Gammon M D (1990) Epidemiology of breast cancer. Epidemiol Rev 12:228-240.

(4) Adami H O, Signorello L B & Trichopoulos D (1998) Towards an understanding of breast cancer etiology. Semin Cancer Biol 8:255-262.

(5) Petrek J A (1994) Breast cancer and pregnancy. J Natl Cancer Inst Monograph No. 16:113-121.

(6) Kelsey J L & Gammon M D (1991) The epidemiology of breast cancer. CA Cancer J Clin 41:146-165.

(7) Kelsey J L & Bernstein L (1996) Epidemiology and prevention of breast cancer. Annu Rev Public Health 17:47-67.

(8) Lambe M, Hsieh C-C, Trichopoulos D et al (1994) Transient increase in the risk of breast cancer after giving birth. N Eng J Med 331:5-9.

(9) Hulka B S & Moorman P G (2001) Breast cancer: hormones and other risk factors. Maturitas 38:103-106.

(10) Key T J (1999) Serum oestradiol and breast cancer risk. Endocrine-Related Cancer 6:175-180.

(11) Wiseman R A (2000) Breast cancer: a single cause for the majority of cases. J Epidemiol Community Health 54:851-858.

(12) Sager R (1997) Expression genetics in cancer: shifting the focus from DNA to RNA. Proc Natl Acad Sci USA 94:952-955.

(13) Zhang L, Zhou W, Velculescu V E et al (1997) Gene expression profiles in normal and cancer cells. Science 276:1268-1272.

(14) Monni O, Hyman E, Moussess S et al (2001) From chromosomal alterations to target genes for therapy: integrating cytogenetic and functional genomic views of the breast cancer genome. Semin Cancer Biol 11:395-401.

(15) Morton NE (1982) Outline of Genetic Epiemiology, Karger, Basel.

(16) Miki Y, Swensen J, Shaattuck-Eidens D et al (1994) A strong candidate for the 17-linked breast and ovarian cancer susceptibility gene BRCA1. Science 266:66-71.

(17) Wooster R, Bignell G, Lancaster K et al (1995) Identification of the breast cancer susceptibility gene BRCA2. Nature 378:789-792.

(18) Hopper J L (2001) Genetic epidemiology of female breast cancer. Semin Cancer Biol 11:367-374.

(19) Easton D F (1999) How many more breast cancer predisposition genes are thee? http://breast-cancer-research.com/vol1no1/23aug99/editorial/1

(20) Strewing J P, Hartge P, Wacholdrer S et al (1997) The risk of cancer associated with specific mutations of BRCA1 and BRCA2 among Ashkenazi Jews. N Eng J Med 336: 1401-1408.

(21) Sirbasku, David A. "Compositions and Methods for the Diagnosis, Treatment and Prevention of Steroid Hormone Responsive Cancers" U.S. patent application Ser. No. 09/852,547 (U.S. Published Application No. 20020006630) and corresponding PCT Published Application No. WO 01/86307.

(22) Sirbasku, David A. "Compositions and Methods for Demonstrating Secretory Immune System Regulation of Steroid Hormone Responsive Cancer Cell Growth" U.S. patent application Ser. No. 09/852,958 (U.S. Published Application No. 20020012954 and corresponding PCT Published Application No. WO 01/85210.

(23) Krajci P, Gedde-Dahl T, Hoyheim B, et al (1992) The gene encoding human transmembrane secretory component (locus poly-Ig receptor) is linked to D1S58 on chromosome 1. Human Genet 90:215-219.

(24) Loupart M-L, Armour J, Walker R et al (1995) Allelic imbalance on chromosome 1 in human breast cancer. I. Minisatellite and RFLP analysis. Genes, Chromosomes & Cancer 12:16-23.

(25) Iau P T, Macmillan R D & Blamey R W (2001) Germ line mutations associated with breast cancer susceptibility. Eur J Cancer 37:300-321.

(26) Cancer Net, A service of the National Cancer Institute (2001). Genetics of Breast and Ovarian Cancer, pp 1-54. http://cancernet.nci.nih.gov/

(27) Oliver M & Hainaut P (2001) TP53 mutation patterns in breast cancers: searching for clues of environmental carcinogenesis. Semin Cancer Biol 11:353-360.

(28) Nelson C L, Sellers T A, Rich S S et al (1993) Familial clustering of colon, uterine, and ovarian cancers as assessed by family history. Genet Epidemiol 10:235-244.

(29) Lynch H T & Lynch J F (1998) Genetics of colon cancer. Digestion 59:481-492.

(30) Lu K H & Broaddus R R (2001) Gynecological tumors in hereditary nonpolyposis colorectal cancer: we know they are common—now what? Gynecologic Oncology 82:221-222.

(31) Garber J E, Goldstein A M, Kantor A F et al (19910 Follow-up study of twenty-four families with Li-Fraumeni syndrome. Cancer Res 51:6094-6097.

(32) Bottomley R H & Condit P T 919680 Cancer families. Cancer Bulletin 20:22-24.

(33) Malkin D (1993) The Li-Fraaumeni syndrome. Cancer: Principles of Oncology Updates 7:1-14.

(34) Eng C, Hampel H & de la Chapelle A (2001) Genetic testing for cancer predisposition. Annu Rev Med 52:371-400.

(35) Eng C, Schneider K, Fraumeni J F & Li F P (1997) Third international workshop on collaborative interdisciplinary studies of p53 and other predisposing genes in LI-Fraumeni syndrome. Cancer Epidemiol Biomark Prevent 6:379-383.

(36) Tsou HC, Teng DH, Ping XL, et al (1997) The role of MMAC1 mutations in early-onset breast cancer: causative in association with Cowden syndrome and excluded in BRCA1-negative cases. Am J Hum Genet 61:1036-1043.

(37) Olopade O I & Weber B L (1998) Breast cancer genetics: toward molecular characterization of individuals at increased risk for breast cancer: part I. Cancer: Principles and Practice of Oncology Updates 12:1-12.

(38) Lynch E D, Ostermeyer E A, Lee M K et al (1997) Inherited mutations in PTEN that are associated with breast cancer, Cowden disease, and juvenile polyposis. Am J Hum Genet 61:1254-1260.

(39) Telatar M, Teroka S, Wang Z et al (1998) Ataxia-telangiectasia gene with a product similar to PI-3 kinase. Science 268:86-97.

(40) Uhrhammer N, Bay J O, Bignon Y J et al (1998) Seventh international workshop on ataxia-telangiectasia. Cancer Res 58:3480-3485.

(41) Swift M, Reitnauer P J, Morrell D et al (1987) Breast and other cancers in families with ataxia-telangiectasia. N Eng J Med 316:1289-1294.

(42) Easton D F (1994) Cancer risks in A-T heterozygotes. Int J Radiation Biol 66:S177-S182.

(43) Fitzgerald M G, Bean J M, Hegde S R et al (1997) Heterozygous ATM mutations do not contribute to early onset of breast cancer. Nature Genetics 15:307-310.

(44) Chen J, Birkholtz G G, Lindblom P et al (1998) The role of ataxia0telangiectasia heterozygotes in familial breast cancer. Cancer Res 58:1376-1379.

(45) Bay J O, Grancho M, Pernin D et al (1998) No evidence for constitutional ATM mutation on breast/gastric cancer families. Int J Oncol 12:1385-1390.

(46) Gastrointestinal Pathology, An Atlas and Text, Fenoglio-Preiser C M (ed), Lippincott-Raven, $2^{nd}$ Edition, (1999); Chapter 20: Carcinomas and other Epithelial and Neuroendocrine Tumors of the Large Intestine, pp 9091068.

(47) Lynch H T, Watson P, Shaw T G et al (1999) Clinical impact of molecular genetic diagnosis, genetic counseling, and management of hereditary cancer. Part II. Hereditary nonpolyposis colorectal carcinoma as a model. Cancer 86 (suppl 11):2457-2463.

(48) Atkin N B (2001) Microsatellite instability. Cytogenet Cell Genet 92:177-181.

(49) Percesepe A, Borghi F, Menigatti M et al (2001) Molecular screening for hereditary nonpolyposis colorectal cancer: a prospective, population-based study. J Clin Oncol 19:3944-3950.

(50) Beckmann M W, Niederacher D, Schnurch H-G et al (1997) Mulitstep carcinogenesis of breast cancer and tumor heterogeneity. J Mol Med (review) 75:429-439.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. The disclosures of all patents, patent applications and publications cited herein are hereby incorporated herein by reference. The discussion of certain references in the Description of Related Art, above, is not an admission that they are prior art to the present invention, especially any references that may have a publication date after the priority date of this application.

What is claimed is:

1. A method to aid in identifying a familial or sporadic pattern of risk in at least one individual for developing breast cancer, the method comprising screening said at least one individual for a mutation in a gene coding for a Poly-Ig (Fc) receptor capable of mediating inhibition of cancer cell growth by an immunoglobulin.

2. The method of claim 1, wherein said screening comprises determining heterozygosity or homozygosity for said mutation.

3. The method of claim 1, wherein said screening comprises determining loss of heterozygosity in the D1S58 locus of chromosome 1.

4. The method of claim 1, wherein said screening comprises detecting an allelic imbalance in the D1S58 locus of chromosome 1.

5. The method of claim 1, wherein screening a control group of individuals known or believed to be at low risk for developing said cancer.

6. The method of claim 5, wherein a predictive relative risk of developing said cancer is in the order homozygous individuals >heterozygous individuals >control individuals.

7. The method of claim 1 comprising screening for a defect in at least one additional gene that is associated with cancer or with an increased risk of developing cancer.

8. The method of claim 1 comprising obtaining a tissue specimen from said at least one individual and testing cells in said specimen for germ line mutations in said gene.

9. The method of claim 1 comprising obtaining a breast cancer specimen from said at least one individual and testing breast cancer cells in said specimen for somatic mutations in said gene.

10. The method of claim 1 comprising obtaining cells from breast fluid and testing said cells for a molecular change in a somatic cell gene coding for a mediator of estrogen reversible cancer cell growth by an immunoglobulin inhibitor.

11. The method of claim 10 comprising detecting a premalignant molecular change in said gene.

* * * * *